United States Patent
Bae et al.

(10) Patent No.: US 10,799,370 B2
(45) Date of Patent: Oct. 13, 2020

(54) INTERVERTEBRAL IMPLANT WITH INTEGRATED FIXATION

(71) Applicant: Howmedica Osteonics Corp., Mahwah, NJ (US)

(72) Inventors: Hyun Bae, Santa Monica, CA (US); Nicholas Slater, Chandler, AZ (US); Joshua A. Butters, Chandler, AZ (US); Dylan Hushka, Chandler, AZ (US); Daniel F. Justin, Orlando, FL (US); Rick B. Delamarter, Los Angeles, CA (US)

(73) Assignee: Howmedica Osteonics Corp., Mahwah, NJ (US)

( * ) Notice: Subject to any disclaimer, the term of this patent is extended or adjusted under 35 U.S.C. 154(b) by 197 days.

(21) Appl. No.: 15/863,013

(22) Filed: Jan. 5, 2018

(65) Prior Publication Data
US 2018/0140439 A1    May 24, 2018

Related U.S. Application Data

(63) Continuation of application No. 14/692,273, filed on Apr. 21, 2015, now Pat. No. 9,861,498, which is a
(Continued)

(51) Int. Cl.
*A61F 2/46* (2006.01)
*A61B 17/16* (2006.01)
(Continued)

(52) U.S. Cl.
CPC ........ *A61F 2/4611* (2013.01); *A61B 17/1671* (2013.01); *A61B 17/8872* (2013.01);
(Continued)

(58) Field of Classification Search
CPC .......... A61B 17/025; A61B 2017/0256; A61F 2/4684; A61F 2/4611
See application file for complete search history.

(56) References Cited

U.S. PATENT DOCUMENTS 3,486,505 A    12/1969    Morrison
3,641,590 A     2/1972    Michele
(Continued)

FOREIGN PATENT DOCUMENTS

EP    0179695 A1    4/1986
EP    1327423 A1    7/2003
(Continued)

OTHER PUBLICATIONS

European Search Report dated Sep. 26, 2012 for PCT/US2010022494.
(Continued)

*Primary Examiner* — Julianna N Harvey
(74) *Attorney, Agent, or Firm* — Lerner, David, Littenberg, Krumholz & Mentlik, LLP

(57) ABSTRACT

A surgical instrument and method are provided for removal of a spinal implant from the intervertebral disc space. The instrument includes a carriage body for interfacing with the implant, a housing for interfacing with the vertebrae, and a handle portion having a first portion rotatably coupled with a proximal end of the housing and a second portion rotatably engageable with a proximal attachment portion of the carriage body. A central passage of the housing extends between the proximal end and a distal engagement surface of the housing. The central passage is dimensioned to mate with the carriage body. Rotation of the handle portion about an axis causes translational movement of the carriage body
(Continued)

along the axis. A modular inserter/distractor apparatus and method and an anchor remover and method are also provided.

15 Claims, 27 Drawing Sheets

Related U.S. Application Data continuation of application No. 13/505,814, filed as application No. PCT/US2010/055259 on Nov. 3, 2010, now Pat. No. 9,033,993.

(60) Provisional application No. 61/257,734, filed on Nov. 3, 2009, provisional application No. 61/257,667, filed on Nov. 3, 2009.

(51) Int. Cl.
    *A61F 2/44* (2006.01)
    *A61B 17/88* (2006.01)
    *A61F 2/30* (2006.01)

(52) U.S. Cl.
    CPC ............ *A61F 2/447* (2013.01); *A61F 2/4684* (2013.01); *A61B 17/1604* (2013.01); *A61F 2/30734* (2013.01); *A61F 2002/305* (2013.01); *A61F 2002/30166* (2013.01); *A61F 2002/30172* (2013.01); *A61F 2002/30367* (2013.01); *A61F 2002/30387* (2013.01); *A61F 2002/30401* (2013.01); *A61F 2002/30522* (2013.01); *A61F 2002/30593* (2013.01); *A61F 2002/30594* (2013.01); *A61F 2002/30738* (2013.01); *A61F 2002/30841* (2013.01); *A61F 2002/30845* (2013.01); *A61F 2002/30879* (2013.01); *A61F 2002/30884* (2013.01); *A61F 2002/30904* (2013.01); *A61F 2002/444* (2013.01); *A61F 2002/4615* (2013.01); *A61F 2002/4619* (2013.01); *A61F 2002/4629* (2013.01); *A61F 2220/0025* (2013.01); *A61F 2220/0033* (2013.01); *A61F 2230/0028* (2013.01); *A61F 2230/0052* (2013.01)

(56) References Cited

U.S. PATENT DOCUMENTS

| | | | |
|---|---|---|---|
| 4,047,524 A | 9/1977 | Hall | |
| 4,501,269 A | 2/1985 | Bagby | |
| 4,681,589 A | 7/1987 | Tronzo | |
| 4,743,262 A | 5/1988 | Tronzo | |
| 4,820,305 A | 4/1989 | Harms et al. | |
| 4,834,757 A | 5/1989 | Brantigan | |
| 4,946,378 A | 8/1990 | Hirayama et al. | |
| 5,192,327 A | 3/1993 | Brantigan | |
| 5,306,309 A | 4/1994 | Wagner et al. | |
| 5,314,477 A | 5/1994 | Marnay | |
| 5,431,658 A * | 7/1995 | Moskovich ........... | A61B 17/025 606/90 |
| 5,443,514 A | 8/1995 | Steffee | |
| 5,443,515 A | 8/1995 | Cohen et al. | |
| 5,507,816 A | 4/1996 | Bullivant | |
| 5,514,180 A | 5/1996 | Heggeness et al. | |
| 5,609,635 A | 3/1997 | Michelson | |
| 5,683,394 A | 11/1997 | Rinner | |
| 5,702,449 A | 12/1997 | McKay | |
| 5,709,683 A | 1/1998 | Bagby | |
| 5,713,899 A | 2/1998 | Marnay et al. | |
| 5,885,299 A | 3/1999 | Winslow et al. | |
| 5,893,889 A | 4/1999 | Harrington | |
| 6,039,762 A | 3/2000 | McKay | |
| 6,096,080 A | 8/2000 | Nicholson et al. | |
| 6,113,638 A | 9/2000 | Williams et al. | |
| 6,120,503 A | 9/2000 | Michelson | |
| 6,235,059 B1 | 5/2001 | Benezech et al. | |
| 6,241,769 B1 | 6/2001 | Nicholson et al. | |
| 6,325,805 B1 | 12/2001 | Ogilvie et al. | |
| 6,336,928 B1 | 1/2002 | Guerin et al. | |
| 6,364,880 B1 | 4/2002 | Michelson | |
| 6,432,107 B1 | 8/2002 | Ferree | |
| 6,447,524 B1 | 9/2002 | Knodel et al. | |
| 6,447,546 B1 | 9/2002 | Bramlet et al. | |
| 6,582,468 B1 | 6/2003 | Gauchet | |
| 6,652,533 B2 * | 11/2003 | O'Neil .................. | A61F 2/4611 606/100 |
| 6,679,887 B2 | 1/2004 | Nicholson et al. | |
| 6,716,245 B2 | 4/2004 | Pasquet et al. | |
| 6,726,720 B2 | 4/2004 | Ross et al. | |
| 6,740,118 B2 | 5/2004 | Eisermann et al. | |
| 6,743,256 B2 | 6/2004 | Mason | |
| 6,767,367 B1 | 7/2004 | Michelson | |
| 6,800,093 B2 | 10/2004 | Nicholson et al. | |
| 7,048,766 B2 | 5/2006 | Ferree | |
| 7,056,344 B2 | 6/2006 | Huppert et al. | |
| 7,056,345 B2 | 6/2006 | Kuslich | |
| 7,060,097 B2 | 6/2006 | Fraser et al. | |
| 7,118,580 B1 | 10/2006 | Beyersdorff et al. | |
| 7,128,761 B2 | 10/2006 | Kuras et al. | |
| 7,204,852 B2 | 4/2007 | Marnay et al. | |
| 7,235,101 B2 | 6/2007 | Berry et al. | |
| 7,320,707 B2 | 1/2008 | Zucherman et al. | |
| 7,331,995 B2 | 2/2008 | Eisermann et al. | |
| 7,364,589 B2 | 4/2008 | Eisermann | |
| 7,503,934 B2 | 3/2009 | Eisermann et al. | |
| 7,503,935 B2 | 3/2009 | Zucherman et al. | |
| 7,588,600 B2 | 9/2009 | Benzel et al. | |
| 7,594,931 B2 | 9/2009 | Louis et al. | |
| 7,611,538 B2 | 11/2009 | Belliard et al. | |
| 7,658,766 B2 | 2/2010 | Melkent et al. | |
| 7,695,516 B2 | 4/2010 | Zeegers | |
| 7,749,271 B2 | 7/2010 | Fischer et al. | |
| 7,763,076 B2 | 7/2010 | Navarro et al. | |
| 7,896,919 B2 | 3/2011 | Belliard et al. | |
| 8,021,403 B2 | 9/2011 | Wall et al. | |
| 8,034,076 B2 | 10/2011 | Criscuolo et al. | |
| 8,083,796 B1 * | 12/2011 | Raiszadeh .............. | A61F 2/447 623/17.11 |
| 8,100,974 B2 | 1/2012 | Duggal et al. | |
| 8,231,676 B2 | 7/2012 | Trudeau et al. | |
| 2002/0004683 A1 | 1/2002 | Michelson | |
| 2002/0035400 A1 | 3/2002 | Bryan et al. | |
| 2002/0116009 A1 * | 8/2002 | Fraser ................... | A61F 2/4611 606/99 |
| 2002/0165613 A1 | 11/2002 | Lin et al. | |
| 2003/0045940 A1 | 3/2003 | Eberlein et al. | |
| 2003/0195517 A1 | 10/2003 | Michelson | |
| 2003/0195632 A1 | 10/2003 | Foley et al. | |
| 2004/0059318 A1 | 3/2004 | Zhang et al. | |
| 2004/0148028 A1 | 7/2004 | Ferree et al. | |
| 2004/0176853 A1 | 9/2004 | Sennett et al. | |
| 2004/0199254 A1 | 10/2004 | Louis et al. | |
| 2004/0220668 A1 | 11/2004 | Eisermann et al. | |
| 2004/0220670 A1 | 11/2004 | Eisermann et al. | |
| 2004/0230307 A1 | 11/2004 | Eisermann | |
| 2004/0260286 A1 | 12/2004 | Ferree | |
| 2005/0004672 A1 | 1/2005 | Pafford et al. | |
| 2005/0033435 A1 | 2/2005 | Belliard et al. | |
| 2005/0043802 A1 | 2/2005 | Eisermann et al. | |
| 2005/0143820 A1 | 6/2005 | Zucherman et al. | |
| 2005/0149192 A1 | 7/2005 | Zucherman et al. | |
| 2005/0149193 A1 | 7/2005 | Zucherman et al. | |
| 2005/0165408 A1 * | 7/2005 | Puno .................... | A61F 2/4611 606/99 |
| 2005/0192586 A1 | 9/2005 | Zucherman et al. | |
| 2005/0216081 A1 | 9/2005 | Taylor | |
| 2006/0004453 A1 | 1/2006 | Bartish et al. | |
| 2006/0085071 A1 | 4/2006 | Lechmann et al. | |
| 2006/0089656 A1 | 4/2006 | Allard et al. | |
| 2006/0116769 A1 | 6/2006 | Marnay et al. | |
| 2006/0129238 A1 | 6/2006 | Paltzer | |
| 2006/0136063 A1 | 6/2006 | Zeegers | |

(56) References Cited

U.S. PATENT DOCUMENTS

| | | |
|---|---|---|
| 2006/0178745 A1 | 8/2006 | Bartish et al. |
| 2006/0195097 A1* | 8/2006 | Evans .................. A61F 2/4611 606/86 A |
| 2006/0212121 A1 | 9/2006 | Ferree |
| 2007/0050032 A1 | 3/2007 | Gittings et al. |
| 2007/0050033 A1 | 3/2007 | Reo et al. |
| 2007/0118145 A1 | 5/2007 | Fischer et al. |
| 2007/0123985 A1 | 5/2007 | Errico et al. |
| 2007/0233244 A1 | 10/2007 | Lopez et al. |
| 2007/0233261 A1 | 10/2007 | Lopez et al. |
| 2007/0239278 A1 | 10/2007 | Heinz |
| 2007/0270968 A1 | 11/2007 | Baynham et al. |
| 2008/0015702 A1 | 1/2008 | Lakin et al. |
| 2008/0051901 A1 | 2/2008 | de Villiers et al. |
| 2008/0051902 A1 | 2/2008 | Dwyer |
| 2008/0097435 A1 | 4/2008 | DeRidder et al. |
| 2008/0109005 A1 | 5/2008 | Trudeau et al. |
| 2008/0154377 A1 | 6/2008 | Voellmicke |
| 2008/0249575 A1 | 10/2008 | Waugh et al. |
| 2008/0269756 A1 | 10/2008 | Tomko et al. |
| 2009/0005870 A1 | 1/2009 | Hawkins et al. |
| 2009/0088849 A1 | 4/2009 | Armstrong et al. |
| 2009/0138015 A1 | 5/2009 | Conner et al. |
| 2009/0164020 A1 | 6/2009 | Janowski et al. |
| 2009/0240333 A1 | 9/2009 | Trudeau et al. |
| 2010/0004747 A1 | 1/2010 | Lin |
| 2010/0185292 A1 | 7/2010 | Hochschuler et al. |
| 2010/0211119 A1 | 8/2010 | Refai et al. |
| 2011/0160866 A1 | 6/2011 | Laurence et al. |
| 2011/0196494 A1 | 8/2011 | Yedlicka et al. |
| 2012/0078371 A1* | 3/2012 | Gamache ........... A61B 17/0682 623/17.16 |
| 2012/0078373 A1 | 3/2012 | Gamache et al. |
| 2012/0116466 A1* | 5/2012 | Dinville ............. A61B 17/7074 606/86 A |
| 2012/0215315 A1 | 8/2012 | Hochschuler et al. |

FOREIGN PATENT DOCUMENTS

| | | |
|---|---|---|
| EP | 1790298 A1 | 5/2007 |
| EP | 1872746 A2 | 1/2008 |
| WO | 03039400 A2 | 5/2003 |
| WO | 03053920 A1 | 7/2003 |
| WO | 2003092507 A2 | 11/2003 |
| WO | 2004071359 A1 | 8/2004 |
| WO | 2004080355 A1 | 9/2004 |
| WO | 2004108015 A2 | 12/2004 |
| WO | 2005051243 A2 | 6/2005 |
| WO | 2006051547 A2 | 5/2006 |
| WO | 2006074414 A2 | 7/2006 |
| WO | 2006086494 A2 | 8/2006 |
| WO | 2007087366 A2 | 8/2007 |
| WO | 2008014453 A2 | 1/2008 |
| WO | 2008021955 A2 | 2/2008 |
| WO | 2010028045 A1 | 3/2010 |

OTHER PUBLICATIONS

Extended European Search Report for Application No. EP16171066 dated Dec. 14, 2016.
International Search Report and Writen Opinion, PCT/US2010/044988, dated Feb. 4, 2011.
International Search Report and Written Opinion for Application No. PCT/US2010/055259, dated Apr. 7, 2011.
International Search Report and Written Opinion, PCT/US2010/22494, dated Oct. 25, 2010.

* cited by examiner

INTERVERTEBRAL IMPLANT WITH INTEGRATED FIXATION

CROSS-REFERENCE TO RELATED APPLICATIONS

The present application is a continuation of U.S. patent application Ser. No. 14/692,273, filed on Apr. 21, 2015, now U.S. Pat. No. 9,861,498, which is a continuation of U.S. patent application Ser. No. 13/505,814, filed on Jun. 19, 2012, now U.S. Pat. No. 9,033,993, which is a national phase entry under 35 U.S.C. § 371 of International Application No. PCT/US2010/055259, filed Nov. 3, 2010, published in English, which claims priority from U.S. Provisional Patent Application No. 61/257,734 filed Nov. 3, 2009, and U.S. Provisional Patent Application No. 61/257,667 filed Nov. 3, 2009, all of the disclosures of which are hereby incorporated herein by reference.

BACKGROUND OF THE INVENTION

The present invention relates to spinal surgery. More particularly, the present invention relates to surgical instruments and methods of using such instruments to insert and remove an implant and anchors with respect to the intervertebral disc space and the adjacent vertebrae.

Back pain can be caused by many different things, including any one of several problems that affect the intervertebral discs of the spine. These disc problems include, for instance, degeneration, bulging, herniation, thinning of a disc, and abnormal movement, and the pain that is experienced is generally attributable to friction or pressure that inevitably occurs when one adjacent vertebra exerts uneven pressure or when both adjacent vertebrae exert such pressure on the disc. Oftentimes, disc problems lead to the vertebrae impinging on one of the very many nerves located in the spinal column.

One surgical method commonly utilized to correct such disc problems is a fusion procedure where a surgeon fuses together adjacent vertebrae in single or multiple levels. Different methods (as well as apparatus for use in those methods) for such surgery have been developed for performance on cervical, thoracic, or lumbar vertebral bodies. These fusion procedures will be referred to herein as interbody fusion or "IF." Traditional IF techniques generally involve removing at least a portion of the troublesome disc from the patient, adding bone graft material into the interbody space between the vertebrae that flank the disc, and inserting a spinal implant device into the space to hold the graft material in place and to support the vertebrae while solid bone mass forms therebetween. Oftentimes, the steps of inserting an implant and bone graft material involve first packing the implant with the bone graft material, and thereafter implanting that construct.

While IF is a long-established technique for correcting the aforementioned disc problems, it is one that is constantly updated. For instance, different implants have been created to suit specific needs, and methods involving the insertion of such implants and the preparation of the vertebrae to receive same are constantly evolving. One major issue that has existed and will continue to exist is the fact that implants inserted into the disc space often take an extended period of time to achieve permanent fusion between the adjacent vertebrae. This leads to long recovery periods for the patient. Certain implants also fail to achieve a degree of fusion that permanently eliminates flexion, extension, and axial movement between the two adjacent vertebrae. This may allow for the initial fusion created by the implant to wear down in certain aspects, which in turn allows for future discomfort to the patient and potentially follow-up surgical procedures.

Thus, there exists a need for a spinal implant, method of using the implant, and related instrumentation for such method that improves upon these shortcomings.

BRIEF SUMMARY OF THE INVENTION

A first aspect of the present invention is a surgical instrument for removing a spinal implant from the intervertebral disc space between two adjacent vertebrae, the instrument including a carriage body having a distal engagement surface for interfacing with the implant and a proximal attachment portion, a housing having a distal engagement surface for interfacing with at least one of the adjacent vertebrae, a proximal end, and a central passage extending between the proximal end and distal engagement surface, the central passage dimensioned to mate with the carriage body, and a handle portion having a first portion rotatably coupled with the proximal end of the housing and a second portion rotatably engageable with the proximal attachment portion of the carriage body, wherein rotation of the handle portion about an axis causes translational movement of the carriage body along the axis.

In accordance with certain embodiments of this first aspect, the first portion of the handle may be rotatably coupled with the proximal end of the housing about one degree of rotational freedom defined by the axis. The proximal attachment portion of the carriage body may include exterior threads and the second portion of the handle may include a bore having internal threads that mate with the external threads. Rotation of the handle portion about the axis may cause relative movement between the internal and external threads and translational movement of the carriage body along the axis with respect to the housing and the handle portion. The carriage body may include a rod extending from the distal engagement surface. The rod may be threadably engageable with a corresponding aperture in the implant. The carriage body may include a knob connected with the rod for threading the rod into the aperture in the implant. The distal engagement surface of the carriage body may be curved according to a contour of the implant. The distal engagement surface of the housing may include first and second feet for interfacing with the superior and inferior adjacent vertebrae, respectively. At least a portion of the central passage may define a first non-circular geometry and at least a portion of an exterior surface of the carriage body may define a second non-circular geometry dimensioned similarly to the first non-circular geometry. The first and second geometries may prevent relative rotation between the housing and the carriage body.

A second aspect of the present invention is a method of removing an implant from the intervertebral disc space between two adjacent vertebrae, the method including the steps of attaching a distal end of a carriage body to the implant, positioning a housing about the carriage body such that a distal surface of the housing contacts at least one of the adjacent vertebrae, and rotating a handle portion rotatably coupled to a proximal end of the housing about a longitudinal axis of the housing such that an internal thread of the handle portion interacts with an external thread on a proximal end of the carriage body, wherein the rotating causes translational movement of the carriage body along the axis with respect to the housing.

In accordance with certain embodiments of this second aspect, the method may further include removing the implant from the disc space through further rotation of the handle. The step of rotating may apply a distal force from the distal surface of the housing onto the at least one of the adjacent vertebrae and a proximal force from the attached distal end of the carriage body onto the implant to remove the implant from the disc space. The step of attaching may include securing the implant to the distal end of the carriage body by inserting a rod of the carriage body into an aperture of the implant. The step of inserting the rod may include screwing a threaded portion of the rod into a threaded portion of the aperture. The step of screwing may include tightening the threaded rod by way of a knob disposed on the carriage body. The step of positioning may include sliding an assembly of the housing and the rotatably attached handle portion over the carriage body. The method may further include the step of engaging the internal thread of the handle portion with the external thread of the proximal end of the carriage body.

A third aspect of the present invention is a surgical instrument for inserting a spinal implant in the intervertebral disc space between two adjacent vertebrae and an anchor engageable with the implant and an adjacent vertebra, the instrument including an engagement body including a superior surface, an inferior surface, a proximal end, a distal engagement surface for interfacing with the implant, and a track on at least one of the superior and inferior surfaces for slidably translating the anchor toward the engagement surface, a handle portion rotatably connectable to the proximal end of the engagement body, a superior distraction rail pivotally connected at a proximal end to a superior portion of the handle portion, and an inferior distraction rail pivotally connected to at a proximal end an inferior portion of the handle portion, wherein rotation of the handle portion about an axis causes translational movement of the engagement body along the axis and contact between the implant and the distraction rails forces distal ends of the rails apart from one another.

In accordance with certain embodiments of this third aspect, the instrument may further include a trial assembly interchangeable with the engagement body, the trial assembly including a trial implant and a body having a proximal end rotatably connectable to the handle portion and a distal end for attachment to the trial implant, the trial implant having a superior surface and an inferior surface, wherein rotation of the handle portion about the axis causes translational movement of the trial assembly along the axis and contact between the trial implant and the distraction rails forces the distal ends of the rails apart from one another. The instrument may further include a plurality of differently sized and shaped trial implants for attachment to the body of the trial assembly, the trial implant selected from the plurality of trial implants. The instrument may further include a rod extending from the engagement surface. The rod may be threadably engageable with a corresponding aperture in the implant. The engagement surface may be curved according to the contour of the implant. The track may be embedded within the surface. The track may include a first track on the superior surface and a second track on the inferior surface.

A fourth aspect of the present invention is a method of inserting an implant in the intervertebral disc space between two adjacent vertebrae and an anchor engageable with the implant and an adjacent vertebra, the method including the steps of attaching a distal end of an engagement body to the implant, connecting a proximal end of the engagement body with a handle portion such that the implant is disposed between superior and inferior distraction rails extending distally from the handle portion, rotating the handle portion about an axis to cause translational movement of the engagement body along the axis and contact between the implant and the distraction rails to force distal ends of the rails apart from one another, inserting the implant into the disc space by rotating the handle portion such that the implant passes distally between the rails and into the disc space, and inserting an anchor into engagement with the implant and the adjacent vertebra.

In accordance with certain embodiments of this fourth aspect, distal ends of the distraction rails may be positioned within the intervertebral disc space, and the step of rotating may actuate the rails to cause distraction of the disc space. The method may further include sliding a tamp along the engagement body in contact with the anchor to force the anchor into engagement with the implant and the adjacent vertebra. The method may further include the step of cutting an entryway into the adjacent vertebra for the anchor by sliding a cutter along the engagement body and piercing the opposing adjacent vertebra.

A fifth aspect of the present invention is a kit of surgical instruments for removing a spinal implant from the intervertebral disc space between two adjacent vertebrae and an anchor engaged with the implant and an adjacent vertebra, the kit including a removal tool having an engagement portion and a handle portion, the engagement portion including a superior surface, an inferior surface, a distal engagement surface for interfacing with the implant, and a track on at least one of the superior and inferior surfaces for slidably translating the anchor away from the engagement surface, and an anchor remover slidably engageable with the removal tool in contact with the anchor to pull the anchor from engagement with the implant and the adjacent vertebra.

In accordance with certain embodiments of this fifth aspect, the kit may include a cutter slidably engageable with the removal tool for piercing an adjacent vertebra to expose the anchor, the cutter having at least one blade edge for cutting bone. The anchor remover and the cutter may be slidably mountable within channels on the removal tool. The anchor remover and the cutter are slidably mountable within the track. The anchor remover may include a distal end having a releasing feature extending from the distal end and configured to engage a locking tab on the anchor to release the tab from interference with the implant. The anchor remover may include a distal end having a grasping feature configured to interface with a catch on the anchor to translate proximal forces from the anchor remover to the anchor. The anchor remover may include a distal end having a releasing feature and a grasping feature, the releasing feature extending from the distal end and configured to engage a locking tab on the anchor to release the tab from interference with the implant, and the grasping feature configured to interface with a catch on the anchor to translate proximal forces from the anchor remover to the anchor.

A sixth aspect of the present invention is a method of removing an anchor from engagement with a vertebral body and an implant disposed in the intervertebral disc space between two adjacent vertebrae, the method including the steps of engaging a distal engagement surface of a removal tool with the implant, the removal tool having superior and inferior surfaces and a track on at least one of the superior and inferior surfaces for slidably translating the anchor away from the engagement surface, sliding an anchor remover distally along the track toward the anchor, sliding a releasing feature of the anchor remover between the implant and a locking tab on the anchor to release the tab from interference with the implant, interfacing a grasping feature of the anchor with a catch on the anchor to translate proximal forces from the anchor remover to the anchor, and applying a proximal force to the anchor remover to pull the anchor from engagement with the implant and the adjacent vertebra.

DETAILED DESCRIPTION

Figure 1:
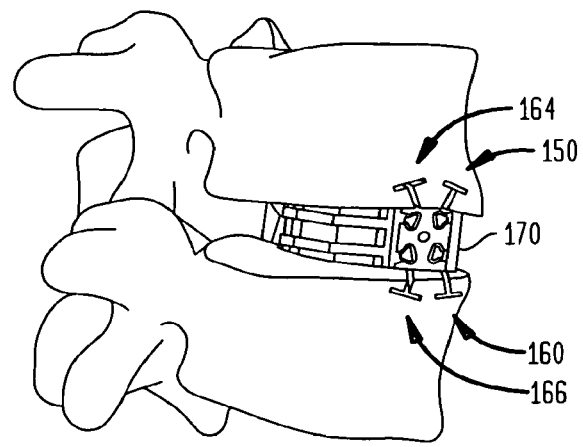
FIG. 1 is a top perspective view of an implant and four anchors inserted into an intervertebral disc space between two adjacent vertebrae in accordance with an embodiment of the present invention.
Figure 2:
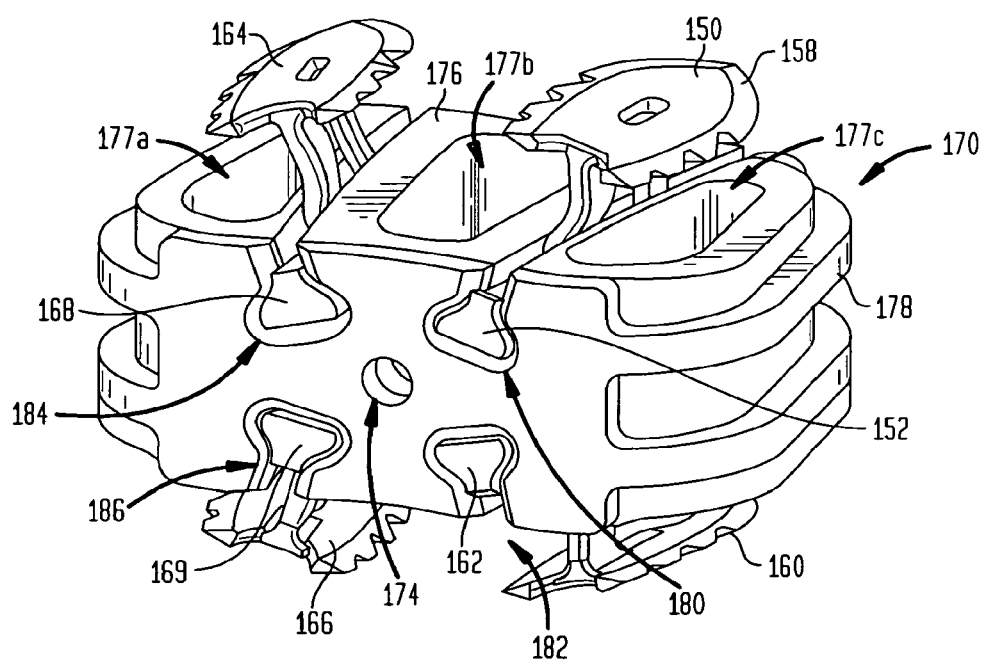
FIG. 2 is a top perspective view of the implant and four anchors shown in FIG. 1.
Figure 3:
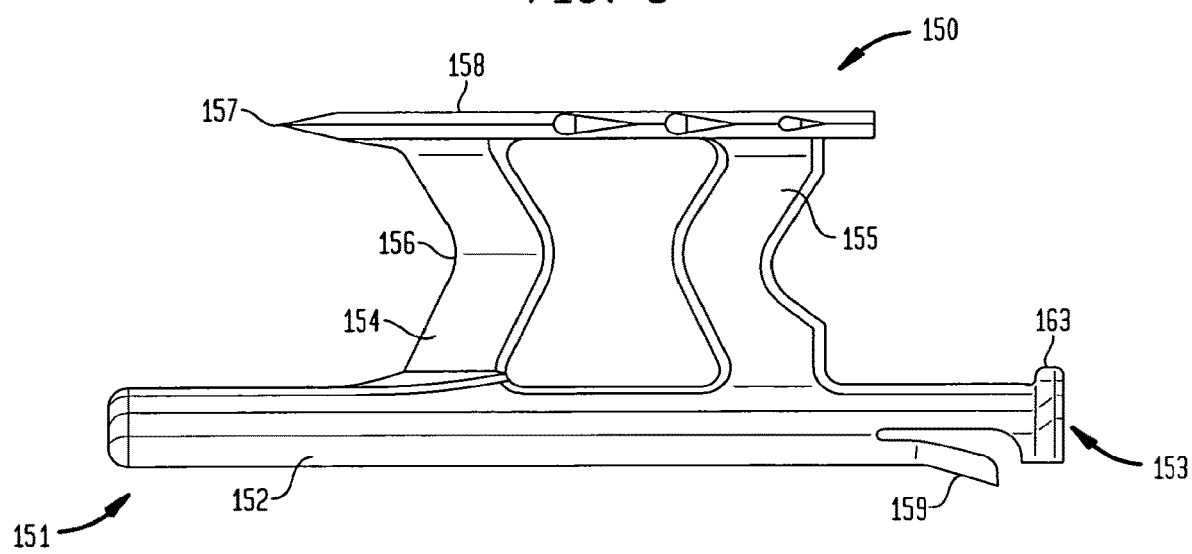
FIG. 3 is a side elevational view of an anchor shown in FIG. 1.
Figure 4:
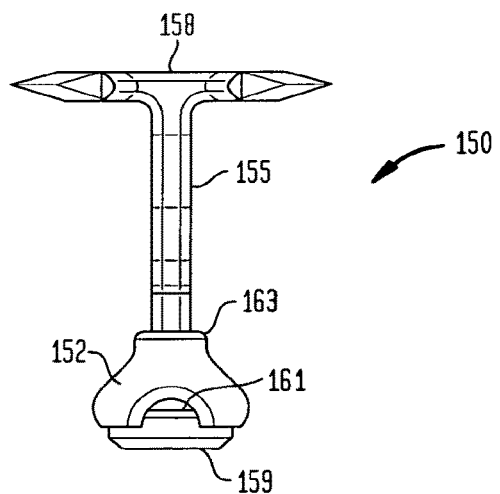
FIG. 4 is a rear elevational view of the anchor shown in FIG. 3.
Figure 4A:
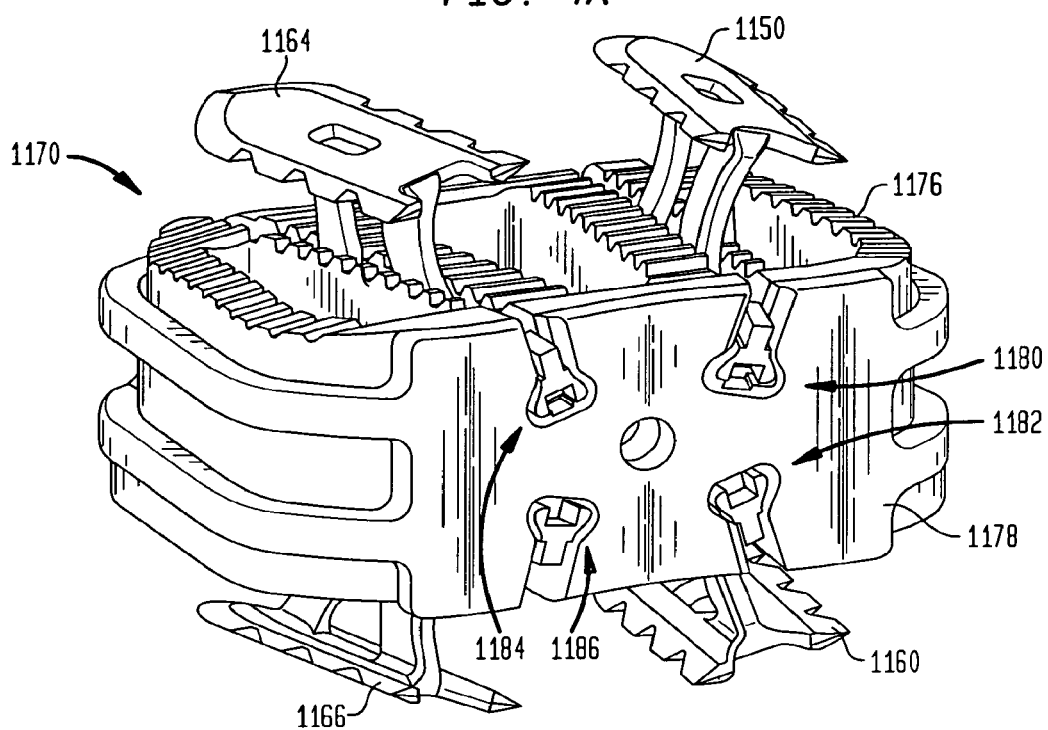
FIG. 4A is a top perspective view of an implant and four anchors in accordance with another embodiment of the present invention.
Figure 4B:
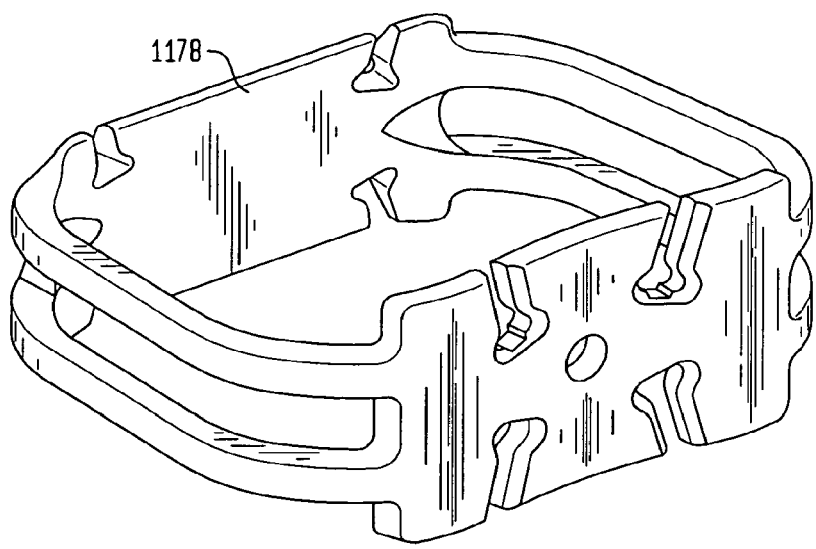
FIG. 4B is a top perspective view of a jacket of the implant shown in FIG. 4A.
Figure 4C:
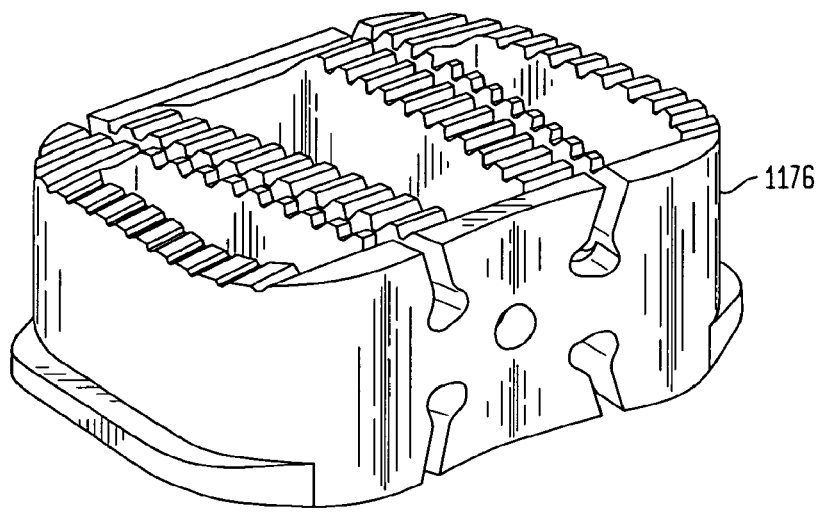
FIG. 4C is a top perspective view of a spacer of the implant shown in FIG. 4A.
Figure 4D:
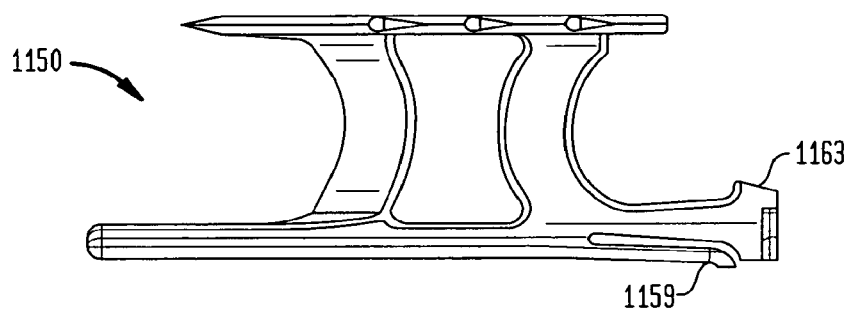
FIG. 4D is a side elevational view of an anchor shown in FIG. 4A.
Figure 4E:
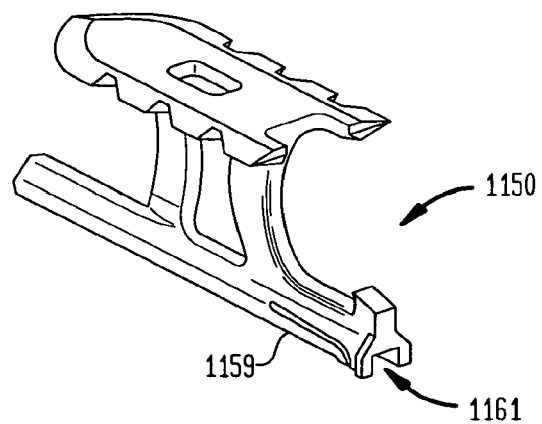
FIG. 4E is a top perspective view of the anchor shown in FIG. 4A.

With reference to certain aspects of the below-described instruments, FIGS. 1-4 show an implant 170 and anchors 150, 160, 164, 166, which are also described more thoroughly in U.S. Non-Provisional patent application Ser. Nos. 12/640,816, 12/640,860, and 12/640,892, the disclosures of which are hereby incorporated by reference herein in their entireties. In the embodiment shown, implant 170 includes, for example, a spacer 176 and a jacket 178 disposed thereabout to provide added strength and support for implant 170. Spacer 176 includes chambers 177a, 177b, 177c that can be packed with graft material. Anchor 150 is essentially identical to anchors 160, 164, 166 and is configured to slidably engage implant 170 and a vertebral body adjacent the intervertebral disc space in which implant 170 is inserted. In the implanted position, anchors 150, 164 are rigidly disposed on opposite sides of implant 170 from anchors 160, 166. Implant 170 includes interconnection features 180, 182, 184, 186 that extend across spacer 176 and jacket 178 to mate with interconnection portions 152, 162, 168, 169, of anchors 150, 160, 164, 166 (best shown in FIGS. 3 and 4), respectively. Interconnection portions 152, 162, 168, 169 preferably transmit tension, compression, shear, torsion, and bending loads between anchors 150, 160, 164, 166 and implant 170, so that spinal loads are distributed from one vertebra to another through anchors 150, 160, 164, 166 and across leading and trailing portions of jacket 178.

As shown, anchor 150 is generally elongate with a leading end 151 and a trailing end 153 opposite therefrom, with interconnection portion 152 extending therebetween. Interconnection portion 152 is shaped and sized to mate with interconnection feature 180 of implant 170 so as to slidably connect anchor 150 with implant 170. Anchor 150 further includes a fixation portion 158 configured as a plate extending between leading and trailing ends 154, 156. Anchor 150 also includes legs 154, 155 extending generally perpendicularly between interconnection portion 152 and fixation portion 158. Leg 154, which is disposed toward leading end 151 of anchor 150, includes a cutting edge 156 and a piercing tip 157 capable of cutting through bone.

On the lower portion of interconnection portion 152 proximate trailing end 153, a locking tab 159 (best shown in FIG. 3) is biased to extend away from interconnection portion 152. Locking tab 159 prevents migration of anchor 150 after it is inserted, and is semi-flexible or otherwise resilient in nature so that it can flex when anchor 150 is inserted and/or removed from implant 170. Preferably, locking tab 159 elastically deforms as anchor 150 is inserted into implant 170 and, once fully inserted past the inner margin of jacket 178, springs back to a position that creates a surface-to-surface contact with jacket 178. The surface-to-surface contact prevents anchor 150 from translating in anterior direction and backing out from its implanted position. Locking tab 159 may alternatively be integrated into jacket 178 or spacer 176. A channel feature 161 is disposed on anchor 150 to allow a remover instrument (described below) to elastically deform the locking feature again for removal from jacket 178. Anchor 150 also possesses a catch feature 163 on trailing end 153 and preferably slanted toward leading end 151 that allows it to interface with the anchor remover instrument. Catch feature 163 is configured as a lip or rim protruding from a surface of anchor 150, and allows for pulling of anchor 150 out of the vertebral body and implant 170 by an anchor remover tool, described below.

A second embodiment of an implant 1170 and anchors anchors 1150, 1160, 1164, 1166 are shown in FIGS. 4A-4E and are similar in nature to the above-described embodiments. Implant 1170 includes spacer 1176 and jacket 1178. Anchor 1150, shown more clearly in FIGS. 4D and 4E, includes a locking tab 1159 and a catch feature 1163 that is more pronounced and leans in a slightly more proximal direction to facilitate a more secure engagement with a removal tool. Interconnection features 1180, 1182, 1184, 1186 may include a slight recess or indent in their periphery to mate with a removal tool, described more fully below. In further embodiments, a locking tab in accordance with the present invention may extend from an anchor in any direction that creates an engagement with the implant, such as an inferior direction as shown above, a medial or lateral direction, or any other direction.

Figure 5:
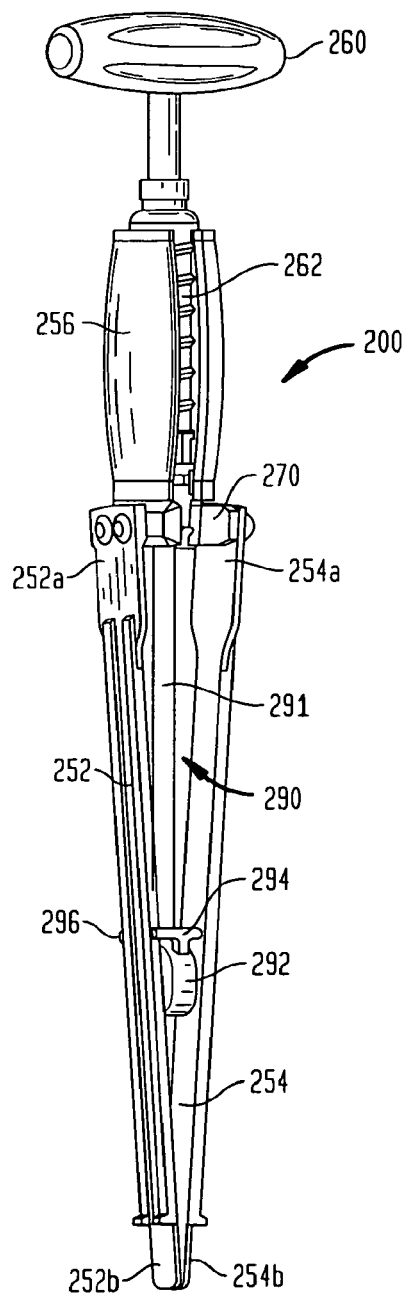
FIG. 5 is a perspective view of a modular inserter/distractor apparatus assembled with a modular trial and trial implant in accordance with another embodiment of the present invention.

In accordance with a first embodiment of the present invention, a set of instruments is shown in FIGS. 5-11 that are configured for installation of an implant 170 and anchors 150, 160, 164, 166. The instruments include a modular inserter/distractor apparatus 200 that facilitates intervertebral distraction during trialing and insertion of implant 170. Apparatus 200 includes two rails 252, 254 having respective proximal ends 252a, 254a and respective distal ends 252b, 254b. Rails 252, 254 are pivotally connected to a handle portion 256 at proximal ends 252a, 254a and are configured such that distal ends 252b, 254b may pivot towards and away from one another. Distal ends 252b, 254b are generally planar so that when in a closed position, as shown in FIG. 5, ends 252b, 254b can be placed within the intervertebral disc space and subsequently forced apart to aid in distracting the space between the adjacent vertebral bodies.

Figure 6:
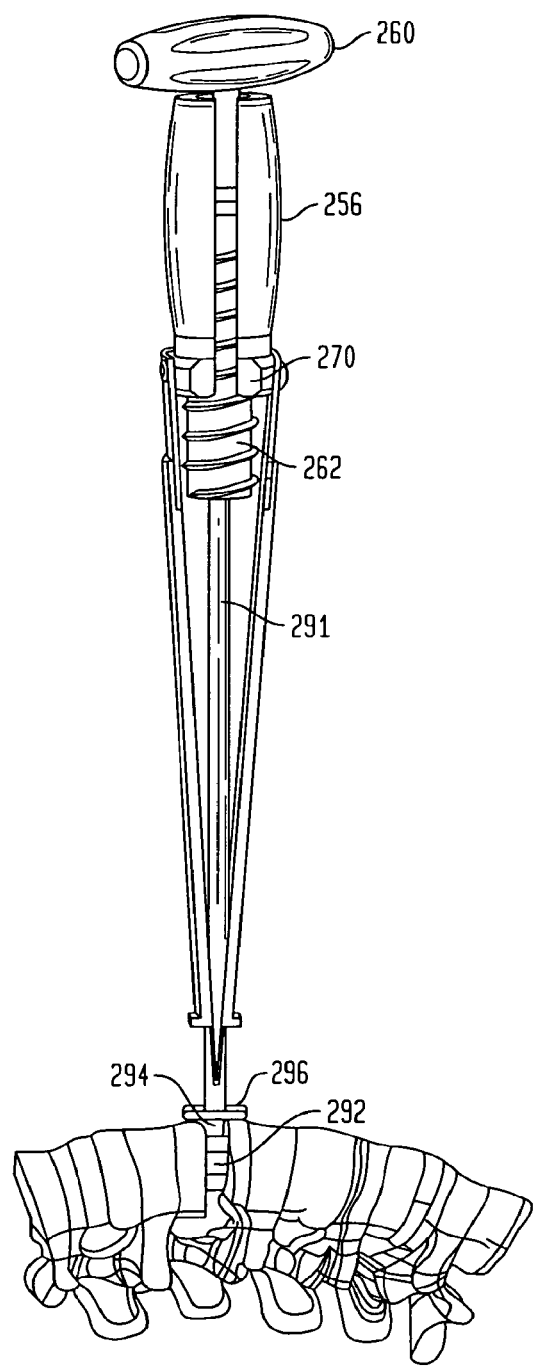
FIG. 6 is a perspective view of the apparatus, modular trial, and trial implant shown in FIG. 5 with the trial implant inserted into an intervertebral disc space.
Figure 7:
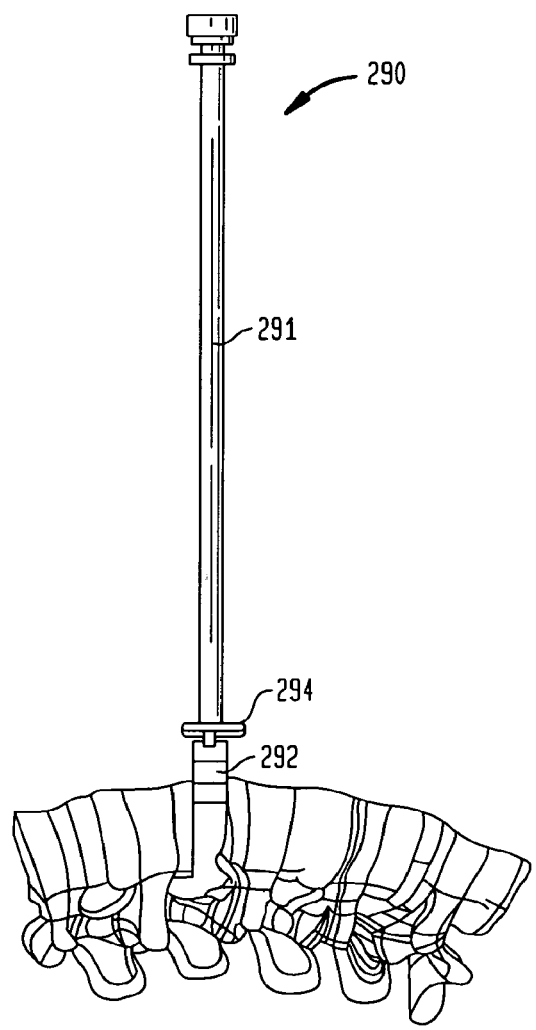
FIG. 7 is a perspective view of the modular trial and trial implant shown in FIG. 5 with the trial implant partially inserted into the intervertebral disc space.
Figure 8:
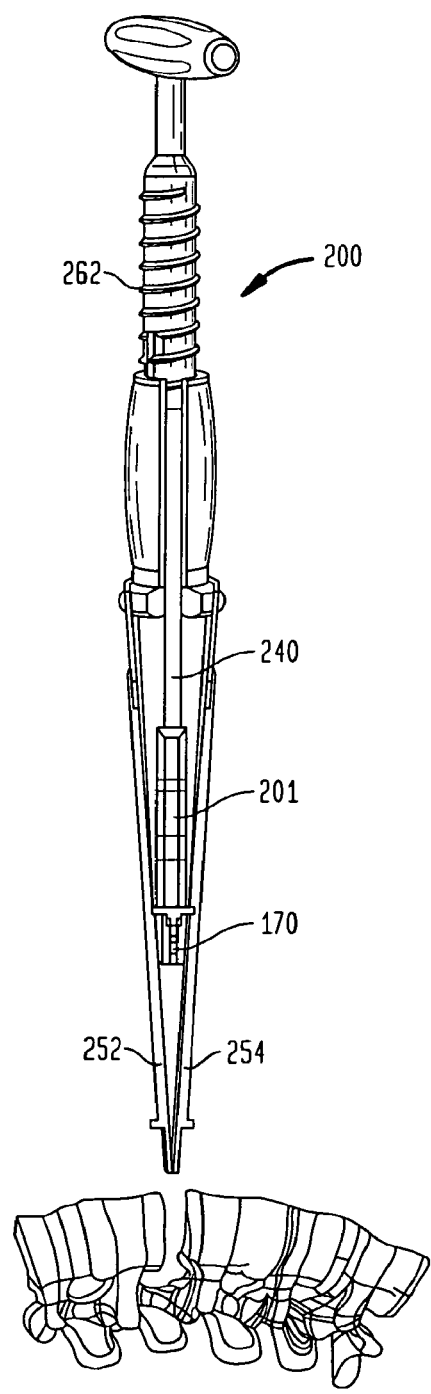
FIGS. 8-11 are perspective views of the apparatus shown in FIG. 5 assembled with a modular inserter guide and the implant shown in FIG. 1.
Figure 9:
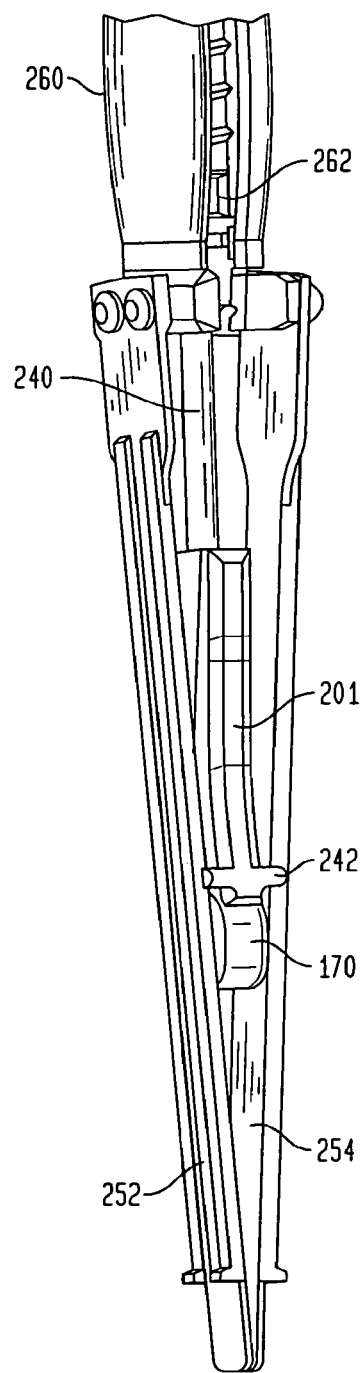

Apparatus 200 is operable with both a modular trial assembly 290 (shown in FIGS. 5-7) and a modular inserter guide 201 (shown in FIGS. 8-11) to cam rails 252, 254 apart, thus creating distraction at the distal end of apparatus 200 as a trial or permanent implant is advanced toward the disc space. Trial assembly 290 includes a shaft 291 that can receive at its distal end a variety of trial implant in various sizes and configurations, such as trial implant 292. Trial implants 292 are utilized to gauge the disc space and select the most appropriately configured permanent implant 170, and can be inserted in a trialing procedure either without apparatus 200, as shown FIG. 7, or with apparatus 200, as shown in FIGS. 5 and 6. At its proximal end, shaft 291 connects with a threaded cylinder 262 that interfaces with mating threads 258 disposed on an inner surface of handle 254. Threaded cylinder 262 can be rotatably coupled with shaft 291 such that cylinder 262 may rotate about a central axis of shaft 291. In such a configuration, shaft 291 and trial implant 292 can maintain their orientation with respect to rails 252, 254 while cylinder 262 is rotated within handle 256.

Trial assembly 290 is preferably be assembled to apparatus 200 by first attaching threaded cylinder 262 to the proximal end of shaft 291, and then passing shaft 291 through a slot 270 in handle 256. Assembly 290 may then be advanced distally to engage threaded cylinder 262 with threads 258 of handle 254. A rotatable knob 260 is provided and is rotatably fixed to a proximal end of threaded cylinder 262. Turning knob 260 allows threaded cylinder 262 to be translated in a proximal or distal direction according to the orientation of the mating threads, thereby also translating trial assembly 290. Rotation of knob 260 can therefore force trial implant 292 toward the disc space. As trial implant 292 is moved distally, the superior and inferior faces thereof contact rails 252, 254, respectively, and force rails 252, 254 apart from one another. Distal ends 252b, 254b of rails, which are in contact with adjacent vertebral bodies, separate from one another, thereby causing distraction of the disc space therebetween.

Once trial implant 292 is moved to a position adjacent distal ends 252b, 254b, stops 294, 296 attached to trial implant 292 engage the adjacent vertebral bodies. Stops 294, 296 are preferably configured to have a height that is greater than that of implant 292 such that the superior and inferior portions of stops 294, 296 will come into contact with the proximal face of the vertebral bodies to prevent over insertion of trial implant 292. As stops 294, 296 encounter the vertebral body, further insertion of implant 292 is prevented, and any further translation of implant 292 with respect to rails 252, 254 results in apparatus 200 moving in a proximal direction with respect to the vertebral bodies and implant 292, as shown in FIG. 6. Continued rotation of knob 260 eventually forces distal ends 252b, 254b out of the intervertebral disc space. Trial assembly 290 may then be disconnected from apparatus 200 to further evaluate the implanted trial implant 292, which is eventually removed in favor of another process of inserting a differently dimensioned trial implant 292 or implant 170. Of course, insertion of trial implant 292 may be interrupted at any point should the size or configuration of implant 292 be deemed unacceptable with respect to the disc space.

Modular inserter guide 201, shown in FIGS. 8-13, is similar in nature to trial assembly 290 in its cooperation with apparatus 200. Guide 201 includes a shaft 240 that connects at its proximal end to threaded cylinder 262. Threaded cylinder 262 is preferably rotatably coupled with shaft 240 such that cylinder 262 may rotate about a central axis of shaft 240. In such a configuration, shaft 240 and implant 170 can maintain their orientation with respect to rails 252, 254 while cylinder 262 is rotated within handle 256.

Modular inserter guide 201 is preferably assembled to apparatus 200 in a similar manner as trial assembly 290, described above. As knob 260 is turned, threaded cylinder 262 is translated in a proximal or distal direction, thereby also translating guide 201 and implant 170. Rotation of knob 260 can therefore force implant 170 toward the disc space. As implant 170 is moved distally, the superior and inferior faces thereof contact rails 252, 254, respectively, and force rails 252, 254 apart from one another. Distal ends 252b, 254b of rails, which are in contact with the adjacent vertebrae, separate from one another, thereby causing distraction of the disc space.

Figure 10:
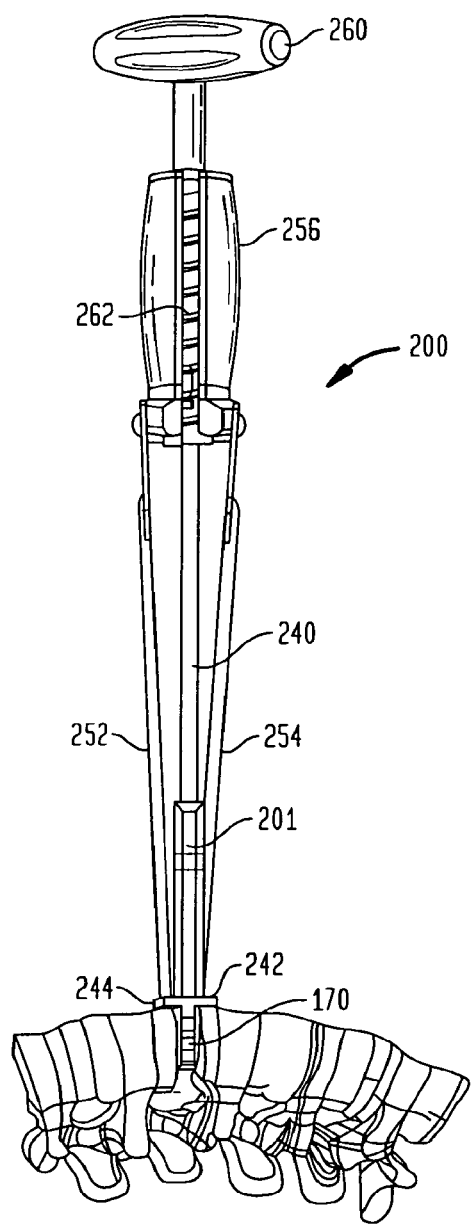
Figure 14:
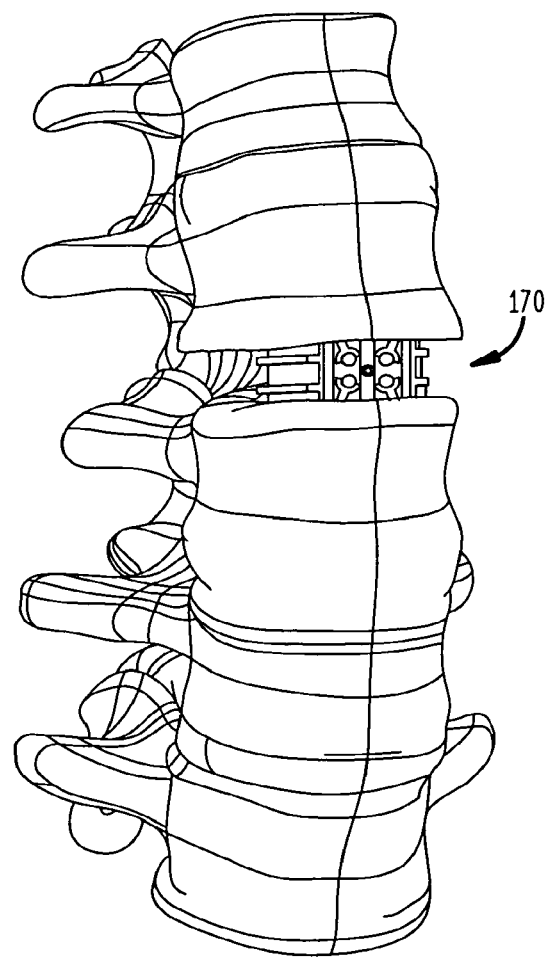
FIG. 14 is another top perspective view of the implant and four anchors shown in FIG. 1 inserted into an intervertebral disc space between two adjacent vertebrae.

Once implant 170 is moved to a position adjacent distal ends 252b, 254b, stops 242, 244 attached to the implant engage the adjacent vertebral bodies, as shown more clearly in FIG. 10. Stops 242, 244 are preferably configured to have a height that is greater than that of implant 170 such that the superior and inferior portions of stops 242, 244 will come into contact with the proximal face of the vertebral bodies to prevent over insertion of implant 170. As stops 242, 244 encounter the vertebral bodies, further insertion of implant 170 is prevented, and any further translation of implant 170 with respect to rails 252, 254 results in apparatus 200 moving in a proximal direction with respect to the vertebral bodies and implant 170. Continued rotation of knob 260 eventually forces distal ends 252b, 254b out of the intervertebral disc space. Implant 170 is then in its fully implanted position, as shown in FIG. 14. As rails 252, 254 are removed from the intervertebral space, threaded cylinder 262 disengages and apparatus 200 can be removed from guide 201.

Shown in FIGS. 8-11, guide 201 is capable of attaching securely to implant 170 and placing it into the intervertebral disc space, delivering the anchors 150, 160, 164, 166, and guiding additional instruments, such as a tamp, cutter, and anchor remover, which are more fully described below. At a distal end 204, guide 201 includes a concavely-curved surface 206 that is preferably shaped to match the curvature of implant 170. Surface 206 can be planar or otherwise shaped to more accurately match the contours of the implant with which it is utilized. A threaded rod 212 extends distally of surface 206, is engageable with a threaded aperture 174 of implant 170, and may be controlled by a rotatable knob (not shown) of guide 201 that allows the user to tighten implant 170 to surface 206 of guide 201, thus securing implant 170 rigidly in all six degrees of freedom with respect to guide 201. Tabs 241a, 241b also protrude from surface 206 and engage with corresponding portions of implant 170 to maintain the relative positioning of implant 170 and guide 201.

Figure 11:
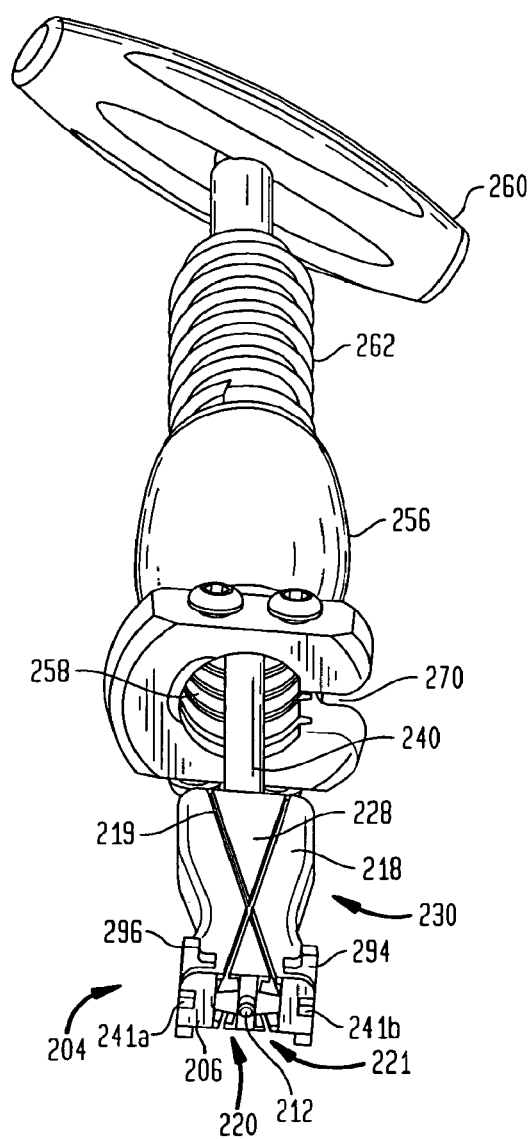

Guide 201 has superior longitudinal channels 218, 219 and inferior longitudinal channels 220, 221 located on superior surface 228 and inferior surface 230, respectively, of guide 201 and being capable of containing, aligning, and slidably delivering anchors 150, 160, 164, 166 to engage with implant 170 and the adjacent vertebral bodies once implant 170 is inserted into the disc space. The pairs of channels 218, 219, 220, 221 cross on their respective surfaces according to the orientation of the anchors 150, 160, 164, 166 with respect to implant 170. Of course, channels 218, 219, 220, 221 may be oriented with respect to their respective surface 228, 230 at any angle with surface 206, and may be crossed, angled, or parallel. Channels 218, 219, 220, 221 may also be angled with respect to their respective surface 228, 230 such that their depth extends along a direction that is perpendicular or angled or canted with their respective surface 228, 230. As shown in FIG. 11, channels 218, 219, 220, 221 are each angled with their respective surface 228, 230. The angles of channels 218, 219, 220, 221 correspond with the orientation of the interconnection features of the implant, and determine the final positioning of the anchors. Channels 218, 219, 220, 221 are also used to guide tamp 600 when tapping the respective anchor into implant 170 and the adjacent vertebra. Tamp 600 accesses channels 218, 219, 220, 221 at a proximal face 242 of distal end 204, shown more clearly in FIG. 12.

Guide 201 is preferably at least somewhat symmetrical about a horizontal plane parallel to and extending between superior and inferior surfaces 228, 230 such that guide 201 may be utilized in the orientation depicted or in an inverted orientation. As implant 170 possesses a similar symmetry, guide 201 can beneficially be connected with implant 170 in either orientation. Guide 201 is also preferably at least somewhat symmetrical about a vertical plane that bisects superior and inferior surfaces 228, 230.

Guide 201 is preferably constructed of metal, and may include two or more metals. For example, distal end 204 may be constructed of stainless steel while handle shaft 240 is constructed of titanium, which may be color anodized. Of course any other material suitable for use during surgery may be employed in the construction of guide 201. Preferably, the materials utilized in the construction of guide 201 are capable of being sterilized multiple times, so that the inserter may be utilized in multiple surgeries/procedures.

Figure 11A:
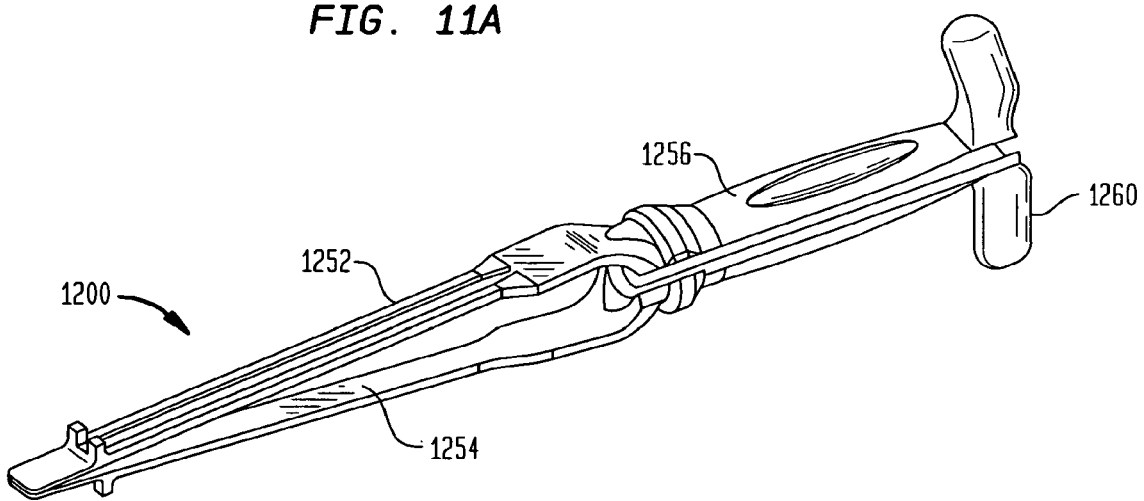
FIGS. 11A-C are perspective views of a modular inserter/distractor apparatus in accordance with another embodiment of the present invention.
Figure 11B:
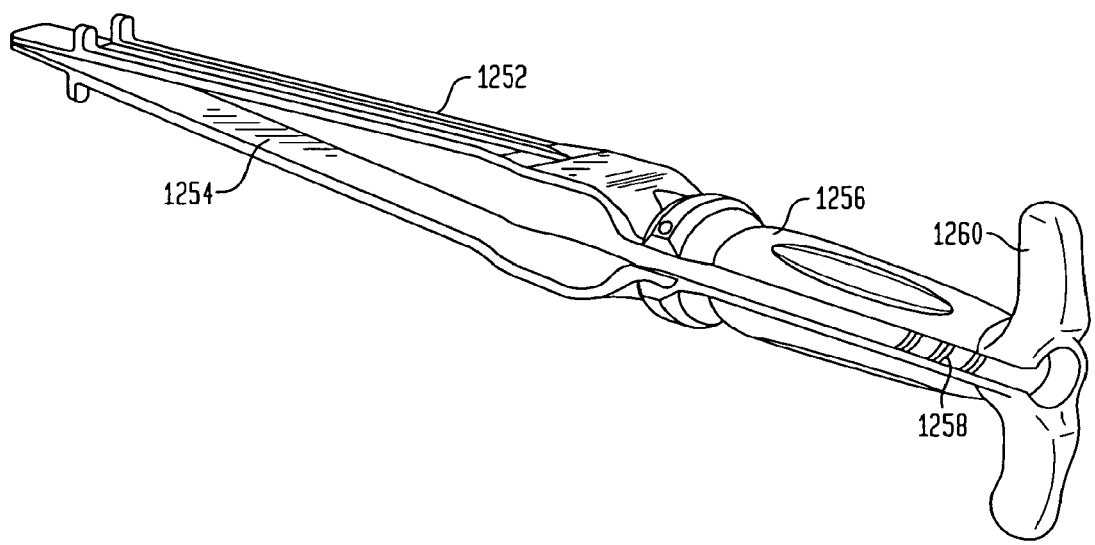
Figure 11C:
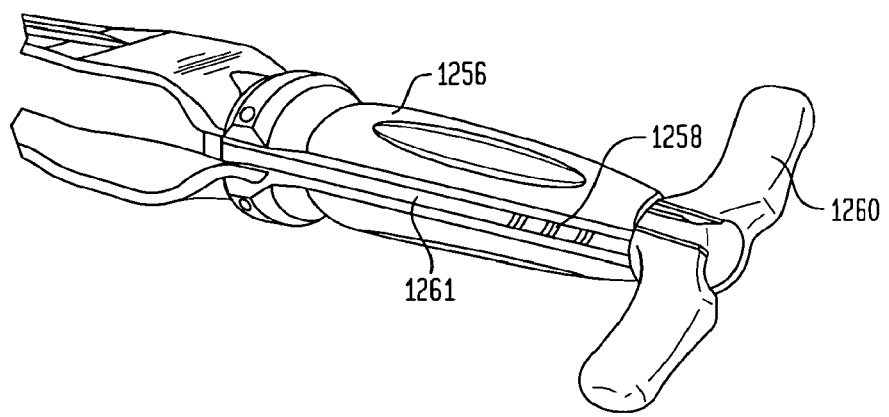

An alternative embodiment of apparatus 200 is shown as apparatus 1200 in FIGS. 11A-C. In this embodiment, rails 1252, 1254 are pivotally and/or flexibly connected to handle 1256, which houses knob 1260. Knob 1260 includes a cylindrical extension 1261 that rotatably connects within handle 1254. An inner surface of extension 1261 includes internal threads 1258 for mating with external threads disposed on a modular inserter guide. The main difference between apparatus 1200 and apparatus 200 is that knob 1206 is the component having internal threads 1258, as opposed to handle 1256. Thus, apparatus 1200 is configured to interact with a modular inserter guide or trial assembly that includes threads on its distal end.

Figure 11D:
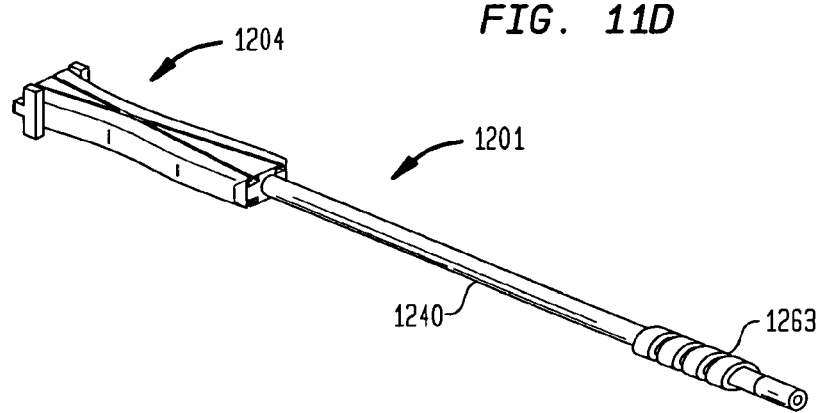
FIG. 11D-F are perspective views of a modular inserter guide in accordance with another embodiment of the present invention.
Figure 11E:
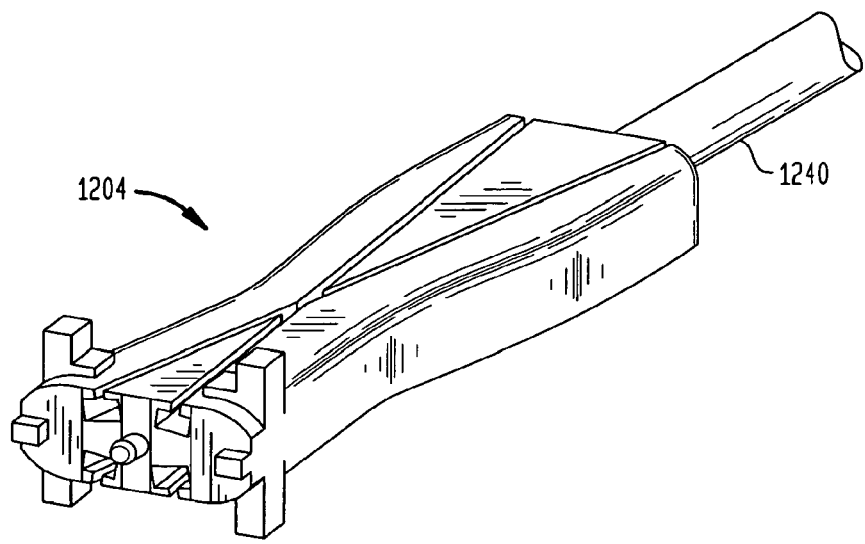
Figure 11F:
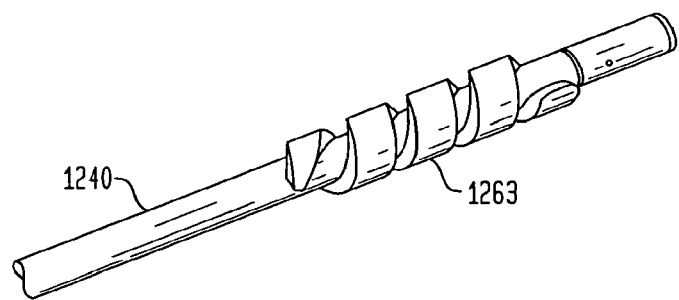
Figure 11H:
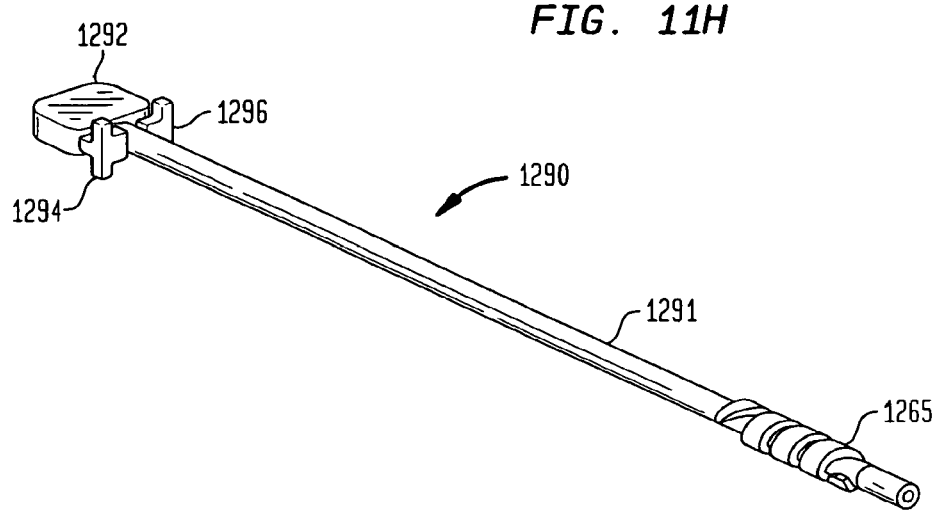
FIG. 11G-H are perspective views of a modular trial and trial implant in accordance with another embodiment of the present invention.
Figure 11G:
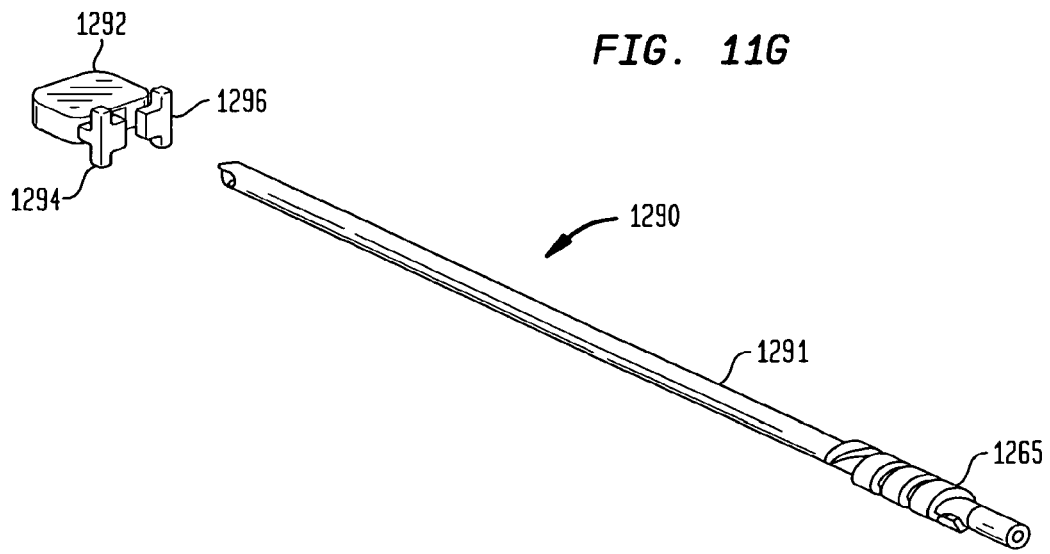

In that respect, an alternative embodiment of guide 201 is shown as modular inserter guide 1201 in FIGS. 11D-F. Guide 1201 is very similar to guide 201 but includes external threads 1263 on a proximal portion of shaft 1240. Similarly, FIGS. 11G and 11H show an alternate embodiment of modular trial 1290 with trial implant 1292. Stops 1294, 1296 are shown connected to trial implant 1292. A proximal portion of shaft 1291 includes external threads 1265. Threads 1263 and 1265 are preferably configured to interact with internal threads 1258 of apparatus 1200.

Figure 12:
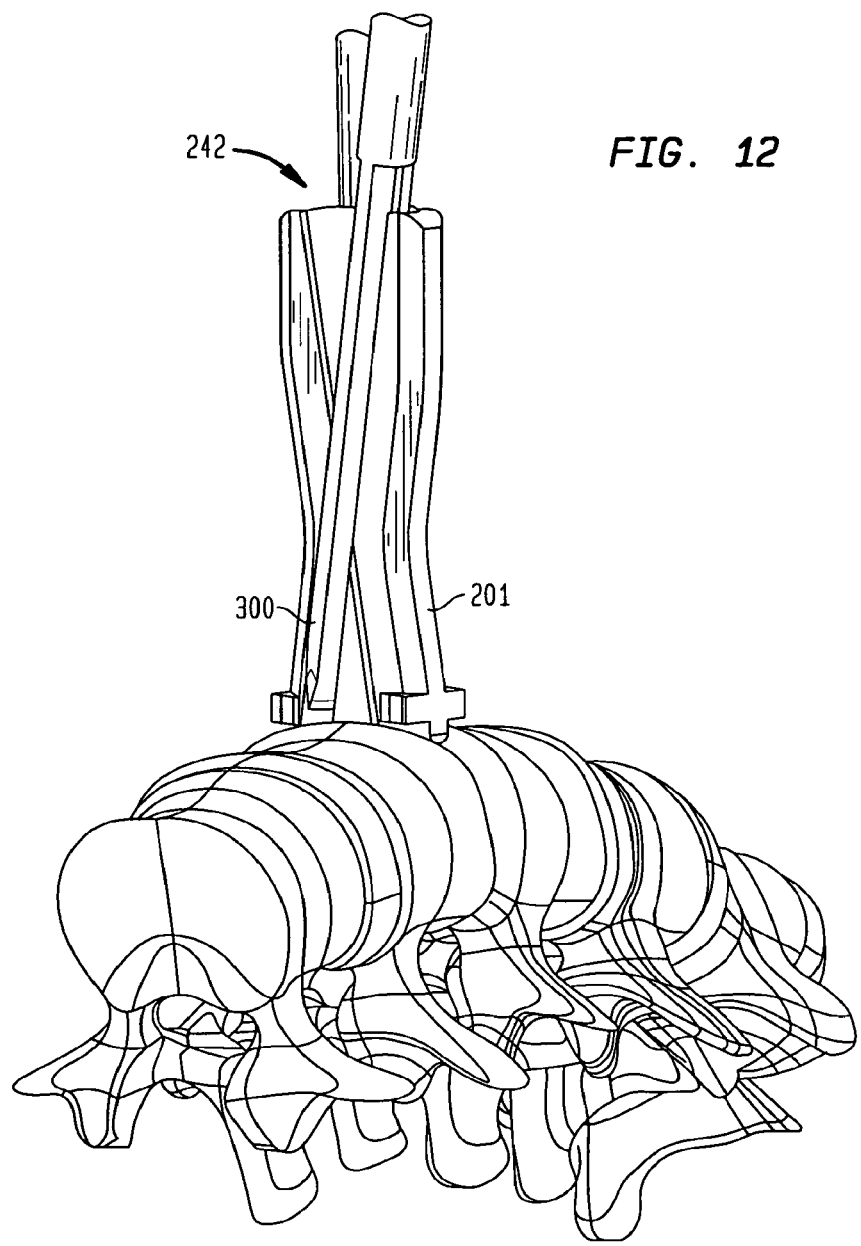
FIG. 12 is a perspective view of a cutter used in connection with the modular inserter guide shown in FIG. 8.
Figure 15:
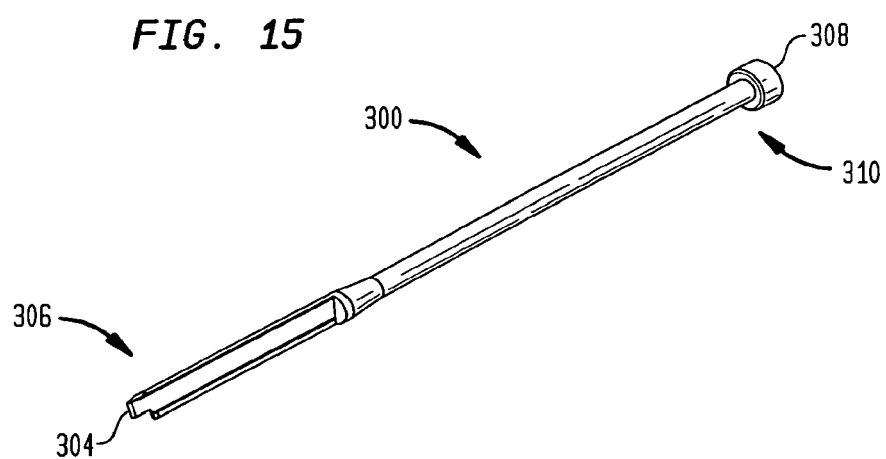
FIGS. 15 and 16 are perspective views of the cutter shown in FIG. 12.
Figure 16:
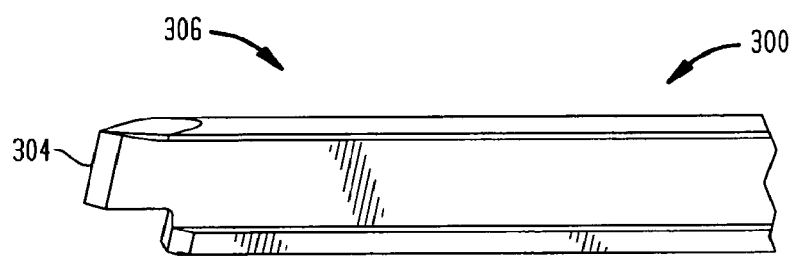

A cutter 300 is shown in FIGS. 15 and 16 and is an elongate instrument preferably constructed of stainless steel. Cutter 300 is primarily used for cutting an initial pathway through the vertebral bodies (as shown in FIG. 12), through which anchors 150, 160, 164, 166 can be led. In particular, cutter 300 is configured to cut a starter channel with minimal force, thereby reducing the total amount of trauma to the vertebral bodies as anchors 150, 160, 164, 166 continue to penetrate the bone. On a distal end 306, cutter 300 includes a blade surface 304. Multiple blade surfaces or needle tips may be included as necessary according to the construction of the associated implant and anchors. Blade surface 304 is similar in geometry to cutting edge 156 of anchor 150, minimizing the total force required to insert anchor 150. Once mated with guide 201, cutter 300 may be impacted on a surface 308 at its proximal end 310, such surface being disposed adjacent to and preferably proximally of the proximal end of guide 201. Impaction of the surface at the proximal end of cutter 300 aids in forcing blade surface 304 into the bone.

Figure 13:
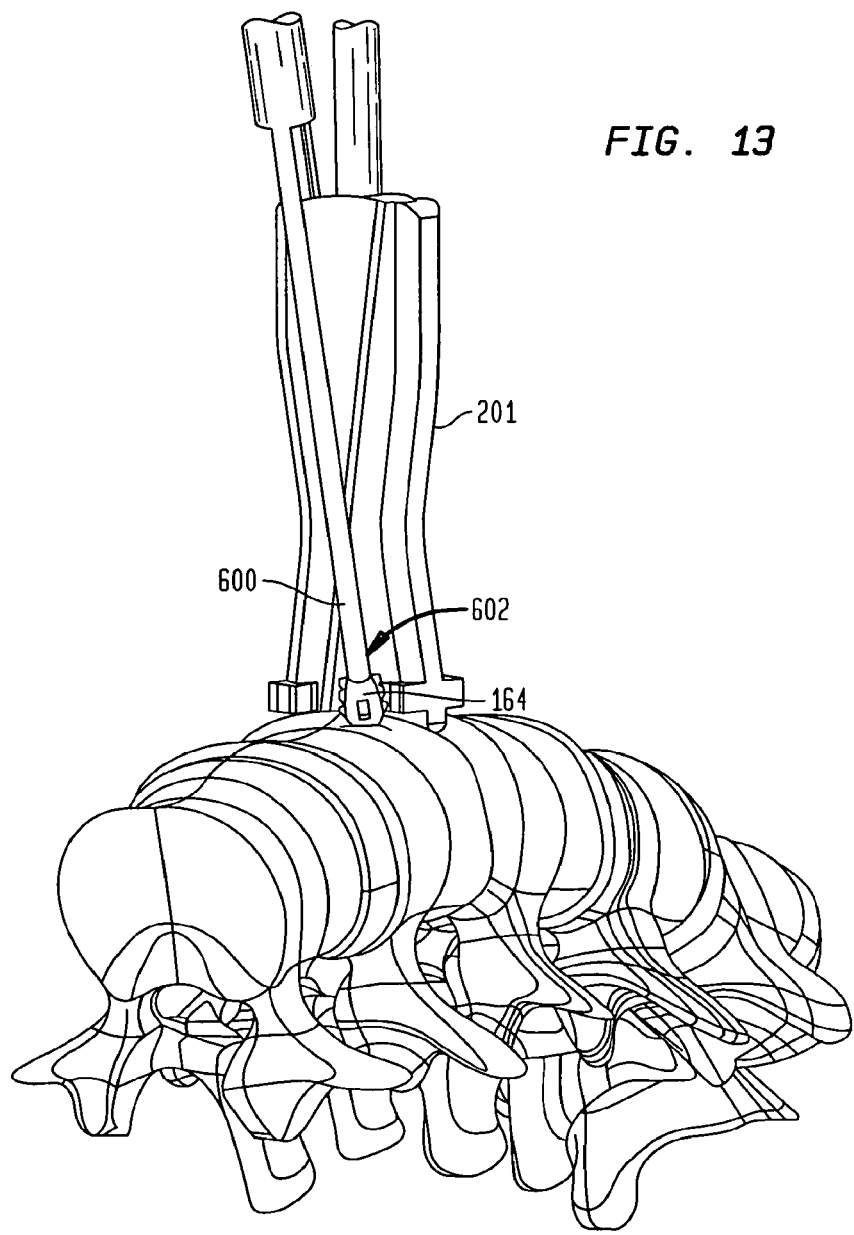
FIG. 13 is a perspective view of an anchor inserted in the intervertebral disc space by the modular inserter guide shown in FIG. 8 and a tamp.
Figure 17:
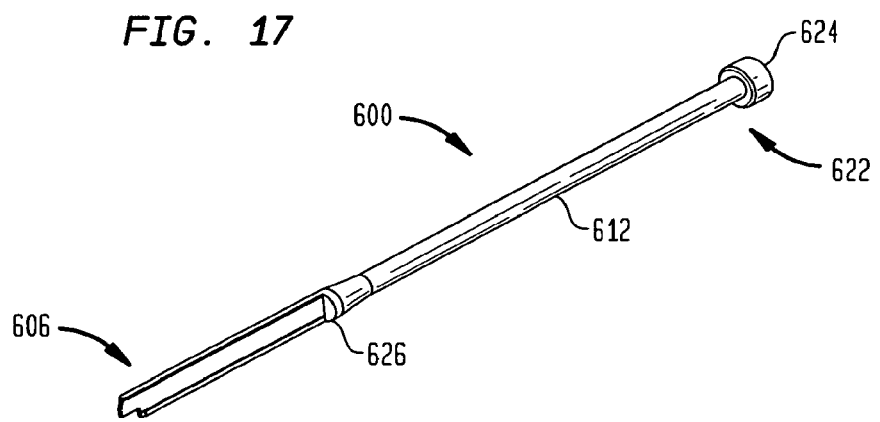
FIGS. 17 and 18 are perspective views of the tamp shown in FIG. 13.
Figure 18:
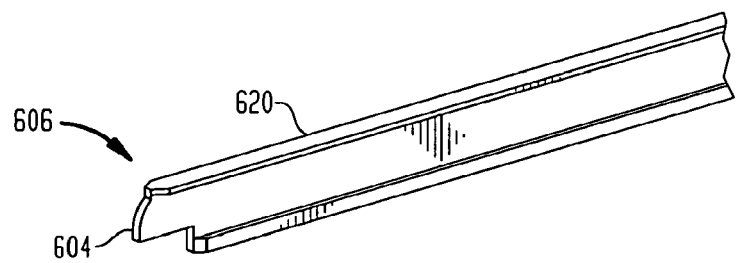

As shown in FIGS. 17 and 18, tamp 600 is a long instrument constructed preferably of stainless steel, and is used primarily for the insertion of anchors 150, 160, 164, 166 into the vertebral bodies (as shown in FIG. 13). Tamp 600 includes a proximal end 622 and a distal end 602 with a lead edge 604 that may or may not match the conforming geometry on the proximal end of anchor 150. When assembled to the guide 201, tamp 600 engages the proximal end of anchor 150 to controllably push anchor 150 into the vertebral body. The mating surfaces between tamp 600 and anchor 150 can be of any configuration as long as tamp 600 may push anchor 150 distally when force is exerted at proximal end 622.

Tamp 600 has a profile that allows it to fit within channels 219, 220, 221, 222. Thus, sliding engagement is permitted between tamp 600 and guide 201 to control the path of tamp 600 during insertion. A stop face 626 is provided that separates distal portion 606 from a main body 612. Stop face 626 is configured to abut face 242 of guide 201 during use of tamp 600 to prevent overinsertion of anchors 150, 160, 164, 166 into the vertebral bodies. Once mated with guide 201, tamp 600 may be impacted on an impaction surface 624 at proximal end 622, as shown in FIG. 17. Impaction of surface 624 aids in forcing distal end 602 of tamp 600, and accordingly, anchors 150, 160, 164, 166 into the bone.

The method of attaching implant 170 to distal end 204 of guide 201 includes inserting a threaded rod 212 into a threaded aperture 174 to secure implant 170 to guide 201 in a particular orientation. Threaded rod 212 may be screwed into aperture 174 by the surgeon actuating a knob. Implant 170 and guide 201 are then secured to one another such that manipulation of guide 201 can ensure proper positioning of implant within the disc space.

The intervertebral disc space is prepared by removing at least a portion of the intervertebral disc material. This can be done at this stage of the procedure or prior to the surgeon's selection or attachment of implant 170. With the appropriate portion of the disc space cleared, the surgeon aligns and inserts implant 170 into the disc space according to the description above respecting apparatus 200. Once implant 170 is fully seated within the disc space according to the above-described method, apparatus 200 may be removed so that guide 201 can be used to facilitate the insertion of anchors 150, 160, 164, 166. To further aid in fusing implant 170 to the adjacent vertebrae, one or more of chambers 177a, 177b, 177c may be packed with bone graft material prior to insertion of implant 170 within the disc space.

At this point, as shown in FIGS. 12 and 13, cutter 300 or, if tamp is provided with the appropriate blades, tamp 600 may be used to cut entryways into the adjacent vertebrae (if so designed). These steps are not necessary, as anchors 150, 160, 164, 166 are configured to pierce the uncut bone.

Anchor 164 is then loaded into longitudinal channel 219, which can also be described as a track on superior surface 228. The method of inserting an anchor according to the present invention is herein described with respect to anchor 164, although more than one anchor may be inserted simultaneously. Interconnection element 152 is disposed within channel 219, and tamp 600 is slidably attached to guide 201 proximal of anchor 164 within channel 219 as well, with least lead edge 604 in contact with the trailing end of anchor 164. As tamp 600 is advanced toward the vertebra, it forces anchor 164 along with it and eventually into contact with the bone. Tamp 600 is further advanced to fully insert anchor 164 into the vertebra such that the interconnection element of anchor 164 locks into place within interconnection feature 184 of implant 170. Stop face 626 may abut surface 242 of guide 201 during advancement to ensure that anchor 164 is not over-inserted. Anchor 164 is eventually seated such that migration and backout are prevented between anchor 164 with respect to both implant 170 and the adjacent vertebra. Thus, axial and torsional movement between implant 170 and the adjacent vertebra are prevented.

Anchors 150, 160, 166 may be inserted in the same manner as described above, although with respect to different channels of guide 201. Tamp 600 may be used first on one anchor and subsequently on the others, or two or more tamps 600 may be utilized together. It is noted that tamp 600 is generally restrained in 5 degrees of freedom with respect to guide 201 during insertion.

After tamp 600 is disengaged from guide 201, threaded rod 212 is unthreaded from implant 170 using the knob. Guide 201 is then removed from the surgical site, leaving implant 170 and anchors 150, 160, 164, 166 in position as shown in FIG. 1. When implant 170 and anchors 150, 160, 164, 166 are implanted from an anterior approach, as shown in FIG. 1, the leading portion of jacket 178 is positioned in the posterior portion of the intervertebral disc space and the trailing portion of jacket 178 is positioned in the anterior portion of the intervertebral disc space. In this arrangement, prosthesis implant 170 and anchors 150, 160, 164, 166 may replicate the strength and stiffness of the natural anterior and posterior longitudinal ligaments to provide superior fixation of adjacent vertebral bodies.

Figure 19:
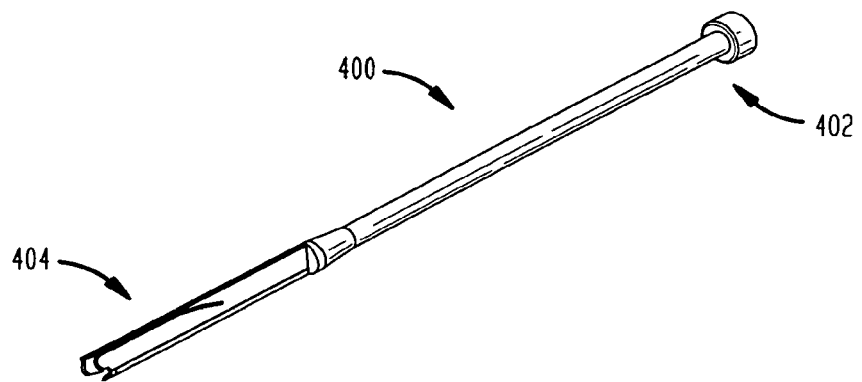
FIGS. 19 and 20 are perspective views of an anchor remover in accordance with another embodiment of the present invention.
Figure 20:
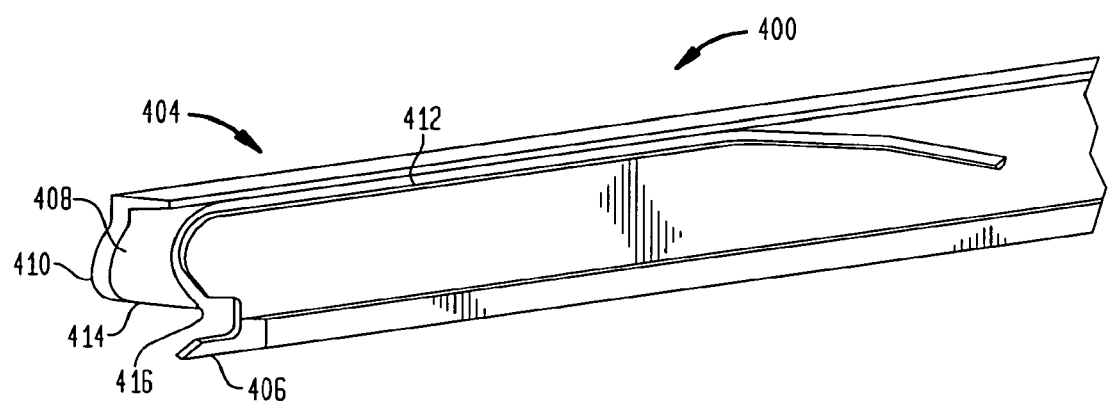

In certain circumstances, one or more of anchors 150, 160, 164, 166 and implant 170 may need to be removed from the patient. For removal of an anchor 150, 160, 164, 166, an anchor remover 400, shown in FIGS. 19 and 20, may be utilized with guide 201. Remover 400 includes a proximal end 402 and a distal end 404. At the distal end 404, the remover 400 includes a releasing feature such as a ramp 406 that engages locking tab 159 on anchor 150 such that it can be released from interference with implant 170, and particularly, jacket 178. Also at distal end 404 is a grasping feature such as a cantilevered hook 408 that mates with a conforming feature, preferably catch 163, on anchor 150 and serves as the pulling surface during removal. Pulling forces applied to anchor remover 400 can thusly be translated to anchor 150. Hook 408 may include a distal blade surface 410 that aids in penetrating bone. Hook 408 is separated from the main body of remover 408 via a slot 412, which allows for hook 408 to move in a superior-inferior direction with some flexibility.

Anchor removal begins with guide 201 attaching onto implant 170. The channels 218, 219, 220, 221 of the guide 201 dictate the trajectory of remover 400 such that it will align with anchor 150, 160, 164, 166 at the end of each channel 218, 219, 220, 221. During anchor removal, cutter 300 may be used to penetrate the vertebral body to gain access to the removal features of anchor 150. Such access is typically needed to penetrate the bone growth accumulated since the original surgical procedure during which implant 170 and anchors 150, 160, 164, 166 were inserted. Once guide 201 is attached to implant 170, remover 400 can be slid distally along the appropriate channel of guide 201 to reach anchor 150. Hook 408 is forced toward trailing end 153 of implant 170. As it approaches, ramp 406 slides between the implant and the inferior-most surface of locking tab 159 to move tab 159 in a superior direction and release it from interference with implant 170. Hook 408 is forced further and to a point where angled surface 414 contacts catch 163. Hook 408 is allowed to flex upward until a hook edge 416 drops down over catch 163. In such a position, hook edge 416 and catch 163 are engaged such that a proximal force on remover 400 will be transferred to anchor 150. A proximal force may then be applied to remover 400 by any known means, including a slide weight or other hammer-like mechanism. Anchor 150 is pulled proximally from the vertebra and along the corresponding channel of guide 201 and removed.

In another embodiment shown in FIGS. 21-26, a removal tool 700 is provided for removing implant 170, with or without attached anchors, from the intervertebral disc space. Tool 700 is preferably utilized with an implant alone, or else with an implant configured with anchors along axes parallel with the proximal-distal axis of implant 170. Anchors that are angled with respect to the proximal-distal axis, such as those with respect to implant 170 above, make removal of the implant and engaged anchors more difficult and such removal may cause additional trauma to the patient. The function of removal tool 700 is to extract the implant with minimal trauma to the patient.

Figure 21:
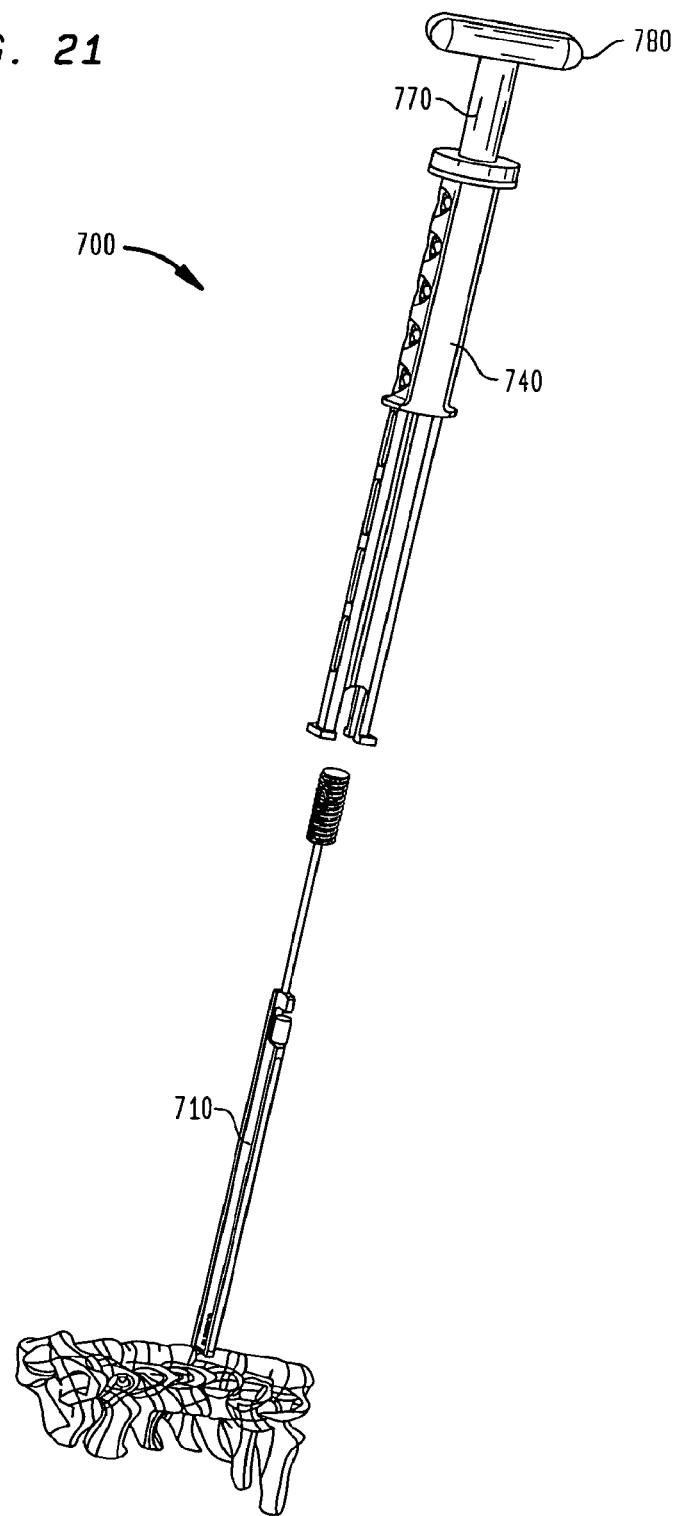
FIG. 21 is a perspective view of a removal tool in accordance with another embodiment of the present invention.
Figure 22:
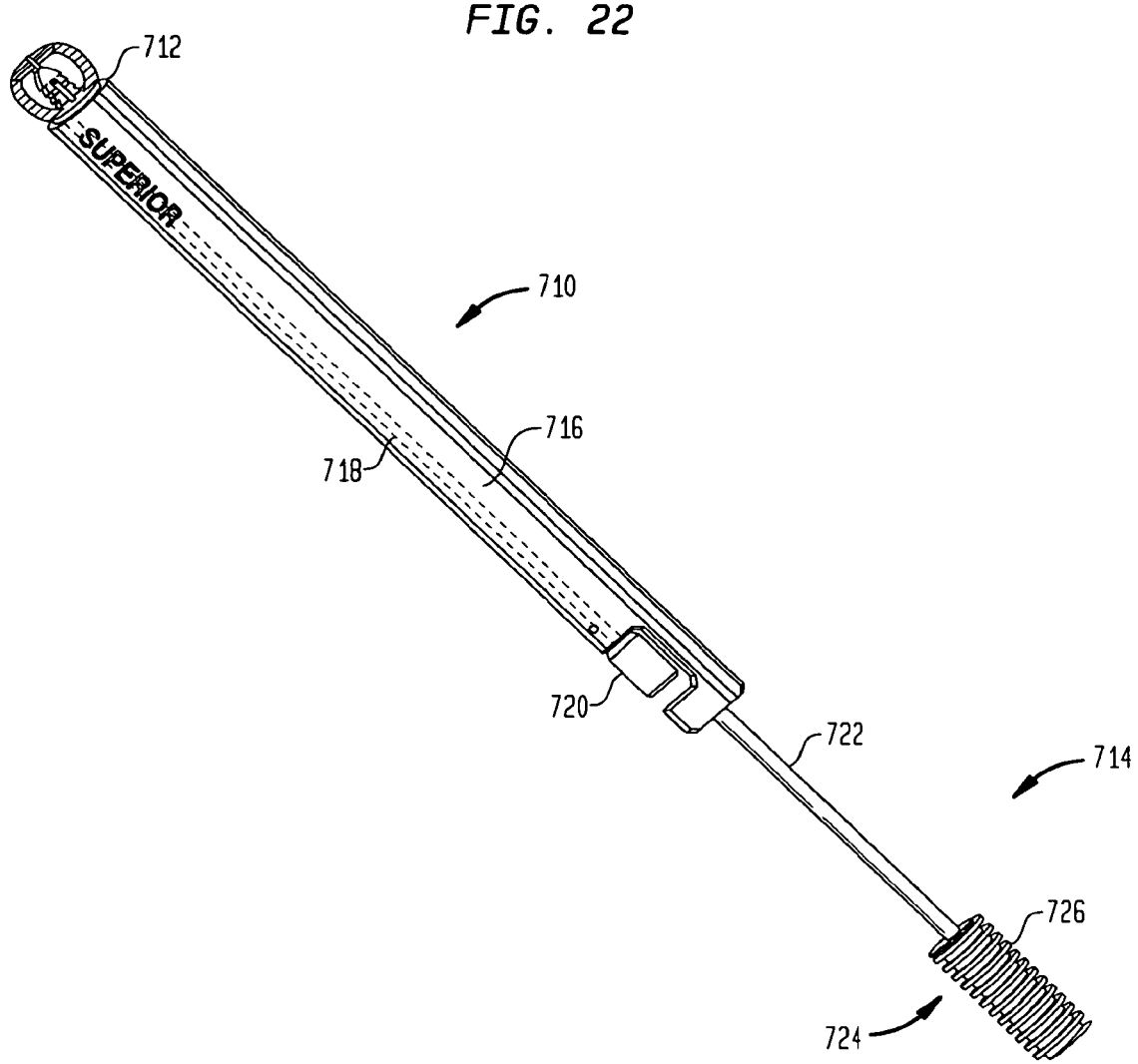
FIG. 22 is a top perspective view of a carriage body of the removal tool shown in FIG. 21.
Figure 23:
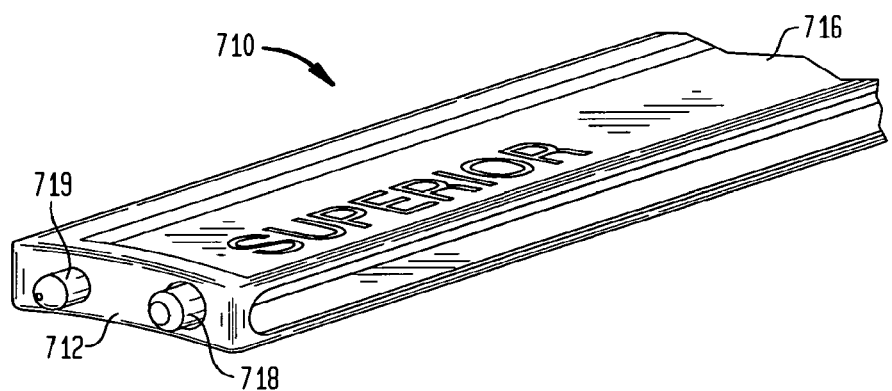
FIG. 23 is a perspective view of the distal end of the carriage body shown in FIG. 21.

As shown in FIG. 21, Removal tool 700 includes a carriage body 710, a housing 740, and a handle portion 770. Carriage body 710, shown more clearly in FIGS. 22 and 23, includes a distal engagement surface 712 for interfacing with implant 170, a proximal attachment portion 714, and a body 716 extending therebetween. Distal engagement surface 712 may be curved according to a contour of implant 170. A rod 718 extends from distal engagement surface 712 and may have threads for engaging with a threaded aperture in the implant, such as aperture 174. A knob 720 is connected with rod 718 for threading rod 718 into aperture 174. Rod 718 is preferably disposed in body 716. An additional post 719 may extend from distal engagement surface 712 for additional engagement with a corresponding feature of implant 170. Proximal attachment portion 714 of carriage body 710 includes a shaft 722 extending from body 716 and a cylindrical portion 724 extending from shaft 722 and having exterior threads 726. Additionally, carriage body 710 may include markings to assist the surgeon in determining the proper positioning of carriage body 710 relative to implant 170 and/or the disc space.

Figure 24:
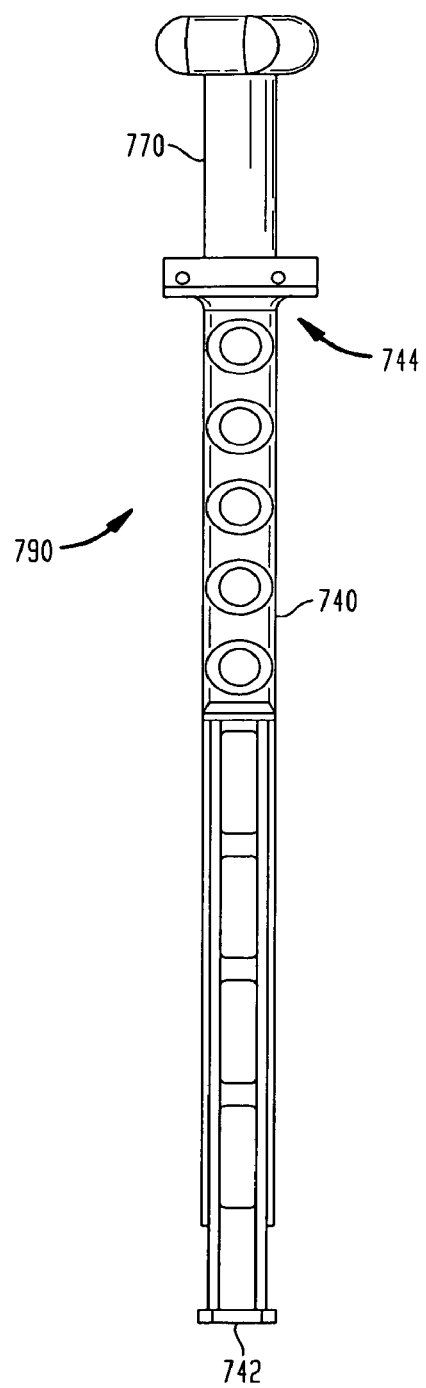
FIG. 24 is a top perspective view of a housing and a handle portion of the removal tool shown in FIG. 21.
Figure 25:
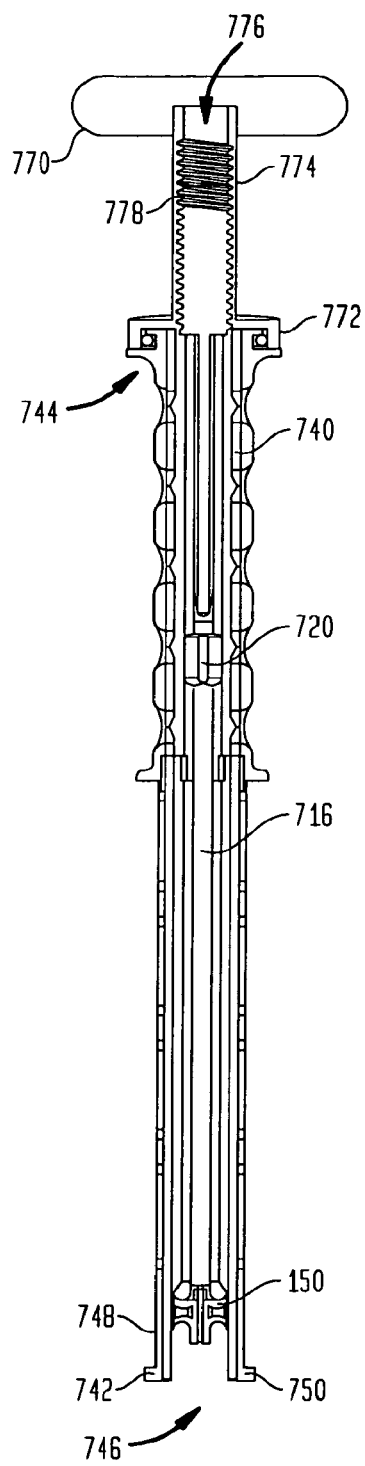
FIG. 25 is a side sectional view of the removal tool shown in FIG. 21.

Shown in FIGS. 24 and 25, housing 740 is tubular in shape and includes a distal engagement surface 742 for interfacing with at least one of the adjacent vertebrae, a proximal end 744, and a central passage 746 extending therebetween. Central passage 746 is dimensioned to slidably mate with the exterior surface of carriage body 710. Distal engagement surface 742 of housing 740 preferably includes first and second feet 748, 750 for interfacing with the superior and inferior adjacent vertebrae, respectively. Feet 748, 750 include relatively large flat surfaces capable of contacting the bony regions of the spine without doing damage to the vertebral body itself or subsiding into the bone. The distal portion of housing 740 is generally rectangular in geometry, while the proximal end is generally circular in cross-section. The proximal circular section forms a cylindrical tube portion with features that are capable of interfacing with handle portion 770.

Handle portion 770, shown in FIGS. 24 and 25, includes a first portion 772 rotatably coupled with proximal end 744 of housing 740 and a second portion 774 rotatably engageable with proximal attachment portion 714 of carriage body 710. First portion 772 is rotatably coupled with proximal end 744 about one degree of rotational freedom defined by a generally longitudinal axis extending along the length of housing 740, while the other two degrees of rotational freedom and the three translational degrees of freedom between handle portion 770 and housing 740 are constrained. The rotatable connection between housing 740 and handle portion 770 is preferably an overlapping or interference fit, such that no translational movement is caused between housing 740 and handle portion 770 when one is rotated with respect to the other. The connection between housing 740 and handle portion 770 preferably causes them to be joined as a housing/handle assembly 790.

Second portion 774 of the handle includes a bore 776 having internal threads 778 that mate with external threads 726 of carriage body 710. Rotation of handle portion 770 about the longitudinal axis of housing 740 causes relative movement between the internal and external threads 778, 726 (when such are engaged) and, thus, translational movement of carriage body 710 along the axis with respect to housing 740 and handle portion 770. Handle portion 770 also includes a grip 780 to be grasped by the surgeon to actuate handle portion 770.

Central passage 746 of housing 740 is dimensioned so that carriage body 710 can slide therein. Preferably, at least a portion of central passage 746 defines a non-circular geometry that mates with a similar non-circular geometry of at least a portion of an exterior surface of carriage body 710. In this way, the mating geometries form a track for carriage body 710 to ride on when carriage body 710 and housing 740 are interfaced. In this configuration, when handle portion 770 is rotated with respect to housing 740, no similar rotation will occur between carriage body 710 and housing 740. Thus, rotation of handle portion 770 will simply cause translational movement of carriage body 710 with respect to housing 740. The non-circular geometries can take on any shape so that relative rotation between housing 740 and carriage body 710 is prevented, such as rectangular, oval, etc.

Figure 26:
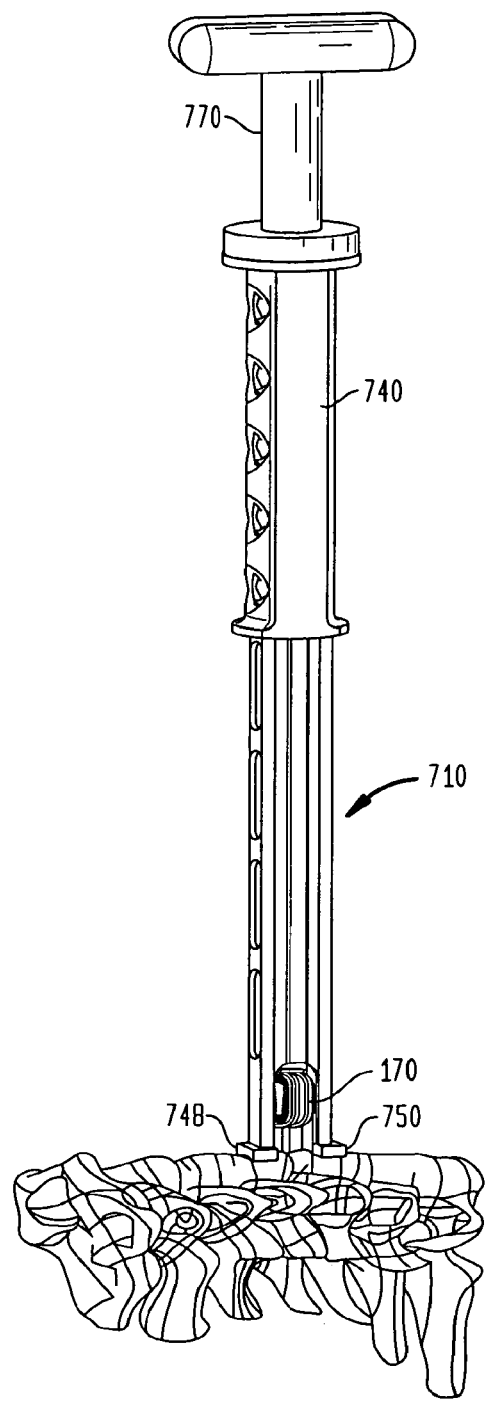
FIG. 26 is a perspective view of the removal tool shown in FIG. 21 used in connection with an implant.

A method of using removal tool 700 includes first attaching distal engagement surface 712 of carriage body 710 to implant 170 while the implant is implanted in the intervertebral space between two vertebrae. Housing/handle assembly 790 is then positioned over carriage body 710 such that distal engagement surface 742 of the housing contacts at least one of the adjacent vertebrae. Feet 748 and 750 are preferably configured to each contact a surface of a vertebral body, as shown in FIG. 26.

Internal threads 778 of handle portion 770 are engaged with external threads 726 of carriage body 710. Handle portion 770 is rotated with respect to proximal end 744 of housing 740 such that internal threads 778 of handle portion 770 interact with external threads 726 of carriage body 710. Such rotation of handle portion 770 causes cylindrical body 724 to translate the axis of housing 740, and thus, causes movement of carriage body 710 and implant 170. The effect of such rotation on the seated implant 170 forces feet 748 and 750 into engagement with the vertebral bodies. Once no further distal movement of housing 740 can occur with respect to the vertebral bodies, further rotation of handle portion 770 causes implant 170 to pull out of the disk space. A distal force from distal engagement surface 742 of housing 740 onto the adjacent vertebrae and a proximal force from the attached distal engagement surface 712 of carriage body 710 onto implant 170 therefore act to remove implant 170 from the disc space. Housing 740 is configured to accept any anchors attached to implant 170 into central passage 746 during removal of implant 170, as shown in FIG. 26. Thus, tool 770 is provided to remove implant 170 through a lead screw mechanism that causes removal of implant 170 via a torque provided by a surgeon. Tool 770 is capable of removing implant 170 without the need to hammer or impact an instrument, thus reducing the trauma to the patient.

In alternative embodiments, tool 700 may be configured to include an impaction or slight weight device in lieu of the screw mechanism. In such an embodiment, a surgeon may hammer on a surface of the tool to remove the implant from the disc space. In another alternative embodiment, the screw mechanism may be replaced with a lever arm and cam arrangement, in which an eccentric cam may be mechanically attached to a relatively long thin lever arm that can be grasped by the surgeon. When the lever arm is pulled, the cam rotates causing the implant to be removed from the disc space.

The instruments according to the present invention are preferably constructed of metal, although other types of materials may be used that give the proper strength to the instruments. Such materials could be hard polymeric materials or other plastics. Of course any other material suitable for use during surgery may be employed in the construction of any of the instruments. Preferably, the materials utilized are capable of being sterilized multiple times, so that the instruments may be utilized in multiple surgeries/procedures.

The above-described devices and methods may be utilized in any interbody fusion procedure, such as ALIF (Anterior Lumbar Interbody Fusion), PLIF (Posterior Lumbar Interbody Fusion), TLIF (Transforaminal Lumbar Interbody Fusion), and lateral interbody fusion approaches. The modular trials and modular inserter guides may be used alone, without the modular inserter/distractor, to insert trials and implants into the disc space.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

INDUSTRIAL APPLICABILITY

The present invention enjoys wide industrial applicability including, but not limited to, systems and methods including surgical instruments for implantation and removal of intervertebral implants.

The invention claimed is:

1. A surgical instrument for inserting a spinal implant in the intervertebral disc space between two adjacent vertebrae and an anchor engageable with the implant and an adjacent vertebra, the instrument comprising:
    an engagement body including a superior surface, an inferior surface, a proximal end, a distal engagement surface for interfacing with the implant, a track embedded within at least one of the superior and inferior surfaces for slidably translating the anchor toward the engagement surface, and a stop extending superiorly or inferiorly from the at least one of the superior and inferior surfaces, respectively;
    a handle portion rotatably connectable to the proximal end of the engagement body; and
    superior and inferior distraction rails each pivotally connected to a proximal end of the handle portion;
    wherein rotation of the handle portion about an axis causes translational movement of the engagement body along the axis to force distal ends of the rails apart from one another.

2. The instrument of claim 1, wherein the proximal end of the engagement body is a shaft.

3. The instrument of claim 1, wherein distal ends of the distraction rails are planar.

4. The instrument of claim 1, wherein the stop is adjacent the distal engagement surface and configured to engage one of the adjacent vertebral bodies.

5. The instrument of claim 4, wherein the stop is configured to contact a proximal face of the one of the adjacent vertebral bodies to prevent over insertion of the implant.

6. The instrument of claim 1, further comprising a trial assembly interchangeable with the engagement body, the trial assembly including a trial implant and a body having a proximal end rotatably connectable to the handle portion and a distal end for attachment to the trial implant, the trial implant having a superior surface and an inferior surface, wherein rotation of the handle portion about the axis causes translational movement of the trial assembly along the axis to force the distal ends of the rails apart from one another.

7. The instrument of claim 6, wherein the proximal end of the trial assembly is a shaft.

8. The instrument of claim 6, wherein the trial implant includes a stop adjacent a distal end thereof that is configured to engage at least one of the adjacent vertebral bodies.

9. The instrument of claim 6, further comprising a plurality of differently sized and shaped trial implants for attachment to the body of the trial assembly, the trial implant selected from the plurality of trial implants.

10. The instrument of claim 1, further comprising a rod extending from the engagement surface.

11. The instrument of claim 10, wherein the distal engagement surface includes a distally extending tab configured to engage the implant.

12. The instrument of claim 1, wherein the engagement surface is curved according to the contour of the implant.

13. The instrument of claim 1, wherein the track includes a first track on the superior surface and a second track on the inferior surface.

14. A surgical instrument for inserting a spinal implant in the intervertebral disc space between two adjacent vertebrae and an anchor engageable with the implant and an adjacent vertebra, the instrument comprising:
    an engagement body including a superior surface, an inferior surface, a proximal end, a distal engagement surface for interfacing with the implant, and a track on at least one of the superior and inferior surfaces for slidably translating the anchor toward the engagement surface;
    a rod extending from the engagement surface, wherein the rod is threadably engageable with a corresponding aperture in the implant,
    a handle portion rotatably connectable to the proximal end of the engagement body; and
    superior and inferior distraction rails each pivotally connected to a proximal end of the handle portion;
    wherein rotation of the handle portion about an axis causes translational movement of the engagement body along the axis to force distal ends of the rails apart from one another.

15. A surgical instrument for inserting a spinal implant in the intervertebral disc space between two adjacent vertebrae and an anchor engageable with the implant and an adjacent vertebra, the instrument comprising:
    an engagement body including a superior surface, an inferior surface, a proximal end, a distal engagement surface for interfacing with the implant, and a pair of tracks on at least one of the superior and inferior surfaces for slidably translating the anchor toward the engagement surface, the tracks crossing each other on the respective surface;
    a handle portion rotatably connectable to the proximal end of the engagement body; and
    superior and inferior distraction rails each pivotally connected to a proximal end of the handle portion;
    wherein rotation of the handle portion about an axis causes translational movement of the engagement body along the axis to force distal ends of the rails apart from one another.

* * * * *